United States Patent [19]

Yu et al.

[11] Patent Number: 5,302,585
[45] Date of Patent: Apr. 12, 1994

[54] USE OF CHIRAL 2-(PHOSPHONOVETHOXY)PROPYL GUANINES AS ANTIVIRAL AGENTS

[75] Inventors: Kuo-Long Yu, Hamden; Joanne J. Bronson, Madison; John C. Martin, Cheshire, all of Conn.

[73] Assignees: Institute of Organic Chemistry and Biochemistry of the Academy of Sciences of the Czech Republic, Prague, Czechoslovakia; Rega Stiching v.z.w., Leuven, Belgium

[21] Appl. No.: 918,507

[22] Filed: Jul. 22, 1992

Related U.S. Application Data

[63] Continuation of Ser. No. 801,338, Dec. 2, 1991, abandoned, which is a continuation of Ser. No. 650,531, Feb. 5, 1991, abandoned, which is a continuation of Ser. No. 513,307, Apr. 20, 1990, abandoned.

[51] Int. Cl.$^5$ .......................................... A61K 31/675
[52] U.S. Cl. .................................................. 514/81
[58] Field of Search ............................................ 514/81

[56] References Cited
U.S. PATENT DOCUMENTS 4,659,825  4/1987  Holy et al. .
4,724,233  2/1988  DeClerq et al. ................ 514/81
4,808,716  2/1989  Holy et al. ..................... 514/81

FOREIGN PATENT DOCUMENTS 253412      1/1988   European Pat. Off. ............ 514/81
269947      6/1988   European Pat. Off. ............ 514/81
WO84/04748 12/1984  PCT Int'l Appl. ................ 514/81
2134907     8/1984   United Kingdom ............... 514/81

OTHER PUBLICATIONS

Chemical Abstracts 109:190136p (1988).
Formula Index vol. 109, 1988, p. 830F (col. 1).
Holy et al, "Synthesis and evaluation of acyclic nucleotide analogs", Chemical Abstract, vol. 111:23866m, (1989).
Martin et al., "Synthesis and antiherpesvirus activity of (S)-1 ((3-hydroxy-2-phosphonylmethoxy)propyl.-)cytosine (HPMPC) and related nucleotide analogues", Nucleosides & Nucleotides, vol. 8(5&6):923-926, (1989).
Rosenberg et al., "Acyclic nucleotide analogs. IV. Phosphonyl methoxyalkyl and phosphonylalkyl derivatives of adenine", Chemical Abstract, vol. 111:174565p, (1989).
DeClerq et al., "(S)-9-(2,3-dihydroxypropyl)adenine: An Aliphatic Nucleoside Analog with Broad-Spectrum Antiviral Activity," Science, 200:563-565 (May 5, 1978).
Yang et al., "New Antiretroviral Acyclic Nucleotide Analog: (R)-2'-Me-PMEG ((R)-N(2-phosphonylmethoxypropylguanine)," Antiviral Research, Program &

(List continued on next page.)

Primary Examiner—Jerome D. Goldberg

[57] ABSTRACT

The present invention provides chiral nucleotide analogs having the Formulas I and II

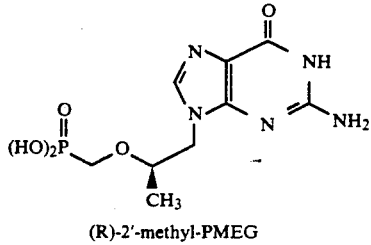

(R)-2'-methyl-PMEG

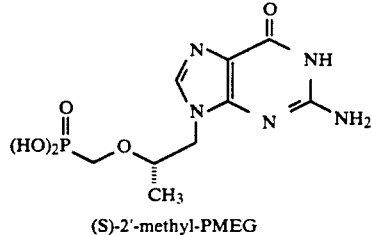

(S)-2'-methyl-PMEG and pharmaceutically acceptable salts and solvates thereof, And their pharmaceutical compositions for use in the treatment of viral infections, especially those caused by human immunodeficiency virus (HIV).

2 Claims, 4 Drawing Sheets

OTHER PUBLICATIONS

Abstracts of 4th International Conference on Antiviral Research, New Orleans, Apr. 21–26, 1991, Abstract 162 on p. 131.

Prisbe et al., "Synthesis and Antiherpes Virus Activity of Phosphate and Phosphonate Derivatives of 9-[(1,3-Dihydroxy-2-propoxy)methyl]guanine," *J. Med. Chem.* (1986) 29:671–675.

DeClerq et al, "A novel selective broad-spectrum anti-DNA virus agent," *Nature* (1986) 323:464–467.

DeClerq et al., "Antiviral activity of phosphonylmethoxyalkyl derivatives of purine and pyrimidines," *Antiviral Research* (1987) 8:261–272.

Holy et al., "3-O-Phosphonylmethyl-9-(S)-(2,3-dihydroxypropyl)adenine novel type of biologially active nucleotide analogue," *Nucl. Acids Res.*, Symposium Series 14 (1984) pp. 277–278.

Bronson et al., "Synthesis and Antiviral Activity of Phosphonylmethoxyethyl Derivatives of Purine and Pyrimidine Bases" *Nucleotide Analogs as Antiviral Agents,* ACS Symposium Series 401 (1989), Chapter 5, pp. 72–87 (Martin, J. C. ed.).

Kim et al., "Acyclic Purine Phosphonate Analogues as Antiviral Agents. Synthesis and Structure-Activity Relationships," *J. Med. Chem.* (1990) 33:1207–1213.

USE OF CHIRAL 2-(PHOSPHONOVETHOXY)PROPYL GUANINES AS ANTIVIRAL AGENTS

This application is related to copending U.S. Ser. No. 08/028,733, which is a continuation of copending application U.S. Ser. No. 07/801,338, filed Dec. 2, 1991, now abandoned, which is a continuation of Ser. No. 07/650,531, filed Feb. 5, 1991, now abandoned, which is a continuation of Ser. No. 07/513,307, filed Apr. 20, 1990, now abandoned.

BACKGROUND OF THE INVENTION

1. Field of the Invention

The present invention relates to certain chiral nucleotide analogs and their compositions and use in the treatment of viral infections. In particular, the present invention relates to certain chiral acyclic treatment of human immunodeficiency virus (HIV) diseases.

2. Information Disclosure Statement

Infectious viral diseases are recognized as an important medical problem. Progress against infectious viral diseases requires the development of drugs with selective antiviral activity while remaining benign to normal cell lines. A number of antiviral agents currently under study, which seem to possess some selectivity, are nucleoside analogs. In general, these compounds are structural analogs of the naturally occurring nucleosides. Structural modification in either the purine or pyrimidine base nucleus and/or the saccharide component results in a synthetically modified nucleoside derivative which, when incorporated into a viral nucleic acid forming process, acts to disrupt further synthesis of viral nucleic acid. Effectiveness of these antiviral agents depends on selective conversion by viral enzymes, but not by host enzymes, to the corresponding nucleotide analog which is then converted to the triphosphate and incorporated into viral nucleic acid. A problem with this antiviral strategy has been the emergence of certain viral strains whose enzymes poorly promote phosphorylation of the nucleoside analogs. To circumvent this problem, intact nucleotide analogs appear to be potentially quite useful as antivirals for incorporation into viral nucleic acid.

Reist and Sturm in PCT/U.S. 84/00737, published Dec. 6, 1984, disclosed new phosphonic acid analogs of nucleoside phosphates which are useful as antivirals for incorporation into viral DNA. The structural formula for these compounds is shown below as Formula 1.

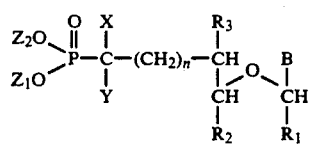

In the Reist compounds, B is a purine or pyrimidine base: $R_1$ and $R_2$ together complete a $\beta$-pentofuranose sugar or $R_1$ is H and $R_2$ is H or hydroxymethyl; $R_3$ is H or OH; X is H, OH, or together with Y is carbonyl oxygen, and Y can also be H; $Z_1$ and $Z_2$ are H or alkyl. These art compounds are generally distinguished from the compounds of the instant invention by (a) the ether-oxygen link to the carbon atom attached to the base which is intended to preserve or mimic the acetal oxygen bond of a pentofuranose sugar ring and (b) the phosphate modification which is a phosphonoalkylene moiety. In contrast, the acyclic sugar analog component of the instant compounds is comprised of an all carbon atom backbone up to a phosphonomethoxy moiety.

Similarly, synthesis and anti-Herpes virus activity of phosphate and phosphonate derivatives of 9-[(1,3-dihydroxy-2-propoxy)methyl]guanine (Formula 2) were disclosed by Prisbe, et al., in *J. Med. Chem.*, 1986, 29, 671.

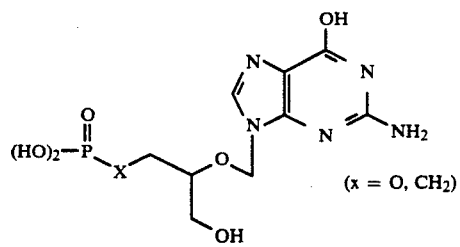

More closely related are adenine phosphonic acid analogs (Formula 3) and their syntheses which were disclosed in the United Kingdom patent application of Holy, et al.. GB 2,134,907A, published on August 22, 1984, and its related U.S. Pat. No. 4,659,825.

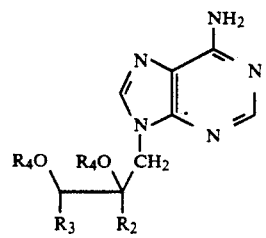

In Formula 3, $R_2$ and $R_3$ may be hydrogen and $R_4$ is independently a hydrogen atom or a $-CH_2P(O)(OH)_2$ group.

A preferred example of one of these compounds, known as (S)-HPMPA (Formula 4), was disclosed by E. DeClercq, et al., in *Nature*, 1986, 323, pp. 464–467, and in *Antiviral Research*, 1987, 8, pp. 261–272, and earlier by A. Holy, et al., *Nucleic Acids Research*, Symposium Series No. 14, 1984, pp. 277–278. The reported antiviral activity of HPMPA resides only in the isomer having the (S)-configuration at the chiral center on the side chain. The corresponding (R)-isomer is reported to be devoid of antiviral activity.

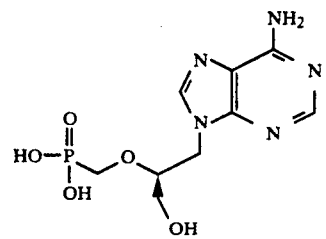

European Patent Application EP-253,412 of A. Holy, et al., published on Jan. 20, 1988, discloses a series of N-phosphonylmethoxyalkyl derivatives of pyrimidine and purine bases (Formula 5) exhibiting antiviral activity

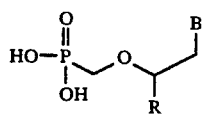

in which R is a hydrogen atom or a hydroxymethyl group and B is an optionally substituted pyrimidin-1-yl, pyrimidin-3-yl, purin-3-yl, purin-7-yl, or purin-9-yl residue, whereby unsubstituted adenin-9-yl is excluded. Substituent B is preferably, inter alia, guanin-9-yl. One of the examples wherein B is guanin-9-yl and R is —CH₂OH (HPMPG) is disclosed only as the racemic (RS)-isomer.

European Patent Application EP-269,947 of R. R. Webb, II, et al., published on Jun. 8, 1988, discloses a series of phosphonomethoxyalkene purine and pyrimidine derivatives which are useful as antiviral agents and have the general Formula 6

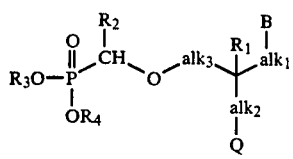

wherein B is a purine or pyrimidine base; alk₁, alk₂, and alk₃ are chemical bonds or alkylene groups; Q is hydrogen or hydroxy; and R₁–R₄ are hydrogen or alkyl, provided that B is not 9-adenyl when R₁–R₄ is hydrogen and alk₁, alk₂, alk₃, and Q are as disclosed by A. Holy, et al., GB 2,134,907, cited above. There is also generically disclosed in European Patent Application EP-269,947 as Example 32 and Example 35 in Table 1 and in claim 8 the racemic compound of the present invention. The racemic compound of the present invention was never made and was suggested as only one of many possible combinations.

In *Nucleotide Analogs as Antiviral Agents;* ACS Symposium Series 401; Martin, J. C. Ed.: Washington, D.C., 1989, Chapter 5, pp. 72–87; J. J. Bronson, et al., report on the series of nucleotide analogs disclosed in the above cited European Patent Application EP-269,947 publication. Also, in *J. Med. Chem.*, 1990, 33, 1207–1213, C. U. Kim, et al., describes a similar series of compounds.

The present applicants have separately prepared the (R)- and (S)-isomers of 9-[2-(phosphonomethoxy)propyl]guanine (2'-methyl-PMEG) and have discovered, surprisingly, that both are active against human immunodeficiency virus (HIV). In sharp contrast, as disclosed in the present invention, both the (R)- and (S)-isomers of HPMPG are inactive against HIV. More surprising was the unexpected finding that the (R)-isomer of 2'-methyl-PMEG provides complete protection of both MT4 and CEM-SS cells against HIV over a concentration range of from about 5 to 100 μM with no observable cytotoxicity at concentrations less than 100 μM. In contrast, PMEG is approximately 30 fold more cytotoxic than (R)-2'-methyl-PMEG.

There is no teaching contained in these references, or combination thereof, which would make obvious the use of the instant compounds against HIV infections. Furthermore, there is no teaching which would suggest the preparation of one specific isomer and that one isomer would provide both unexpected lower toxicity and greater selectivity as an anti-HIV agent.

SUMMARY OF THE INVENTION

The present invention relates to the selective preparation of the (R)- and (S)-isomers of 9-[2-(phosphonomethoxy)propyl]guanine, which are also designated herein as 2'-methyl-PMEG. These compounds differ from the natural nucleotides by having structural variations in their sugar analog component and in the nature of the oxygen-carbon-phosphorous bonds. The compounds of this invention are represented by structural Formulas I and II.

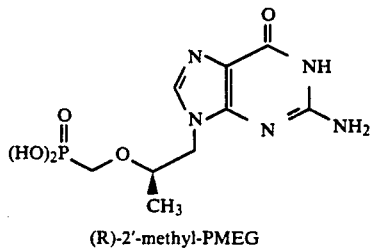

(R)-2'-methyl-PMEG

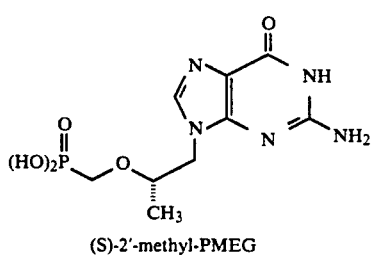

(S)-2'-methyl-PMEG

The present invention also relates to the treatment of viral infections in mammals, including humans, and, in particular, those caused by human immunodeficiency virus (HIV) with a therapeutically-effective amount of a compound of Formulas I or II, and pharmaceutically acceptable salts thereof. This invention further relates to the formulation of these compounds into pharmaceutical compositions and the use of these compositions to treat viral infections.

DETAILED DESCRIPTION OF THE INVENTION

Figure 1:
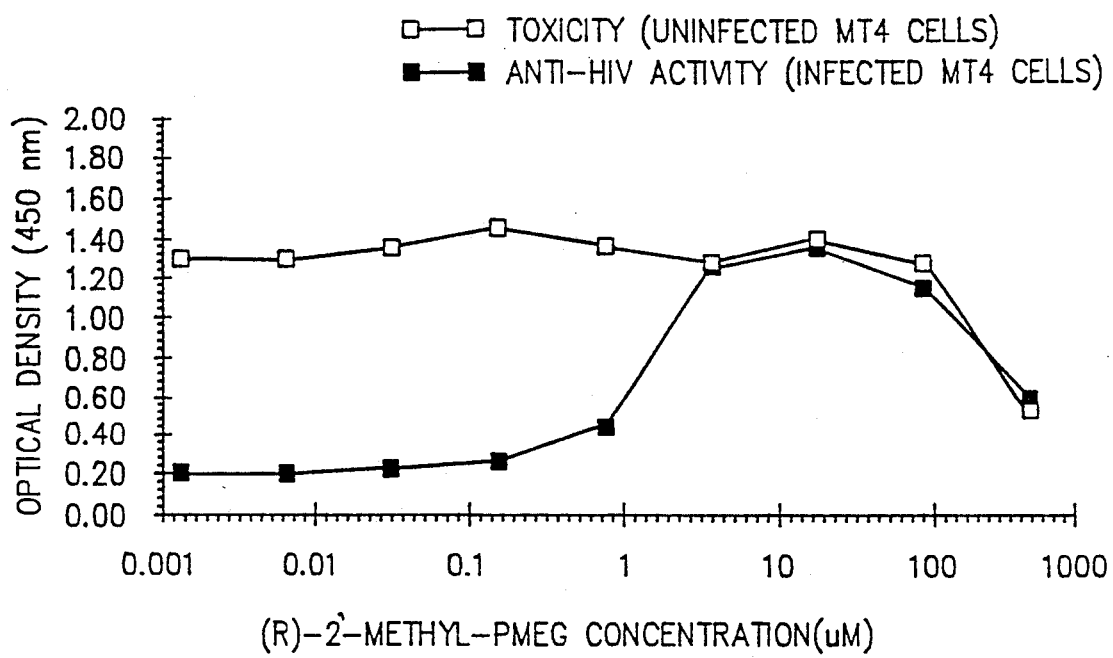
FIG. 1 illustrates the relative effects between cellular toxicity of uninfected and anti-HIV activity of infected MT4 cells by increasing concentrations of (R)-2'-methyl-PMEG (Compound I).

The present invention relates to the stereospecific synthesis of both the (R) and (S) chiral isomers of compounds of Formulas I and II, respectively, and to pharmaceutically acceptable salts thereof.

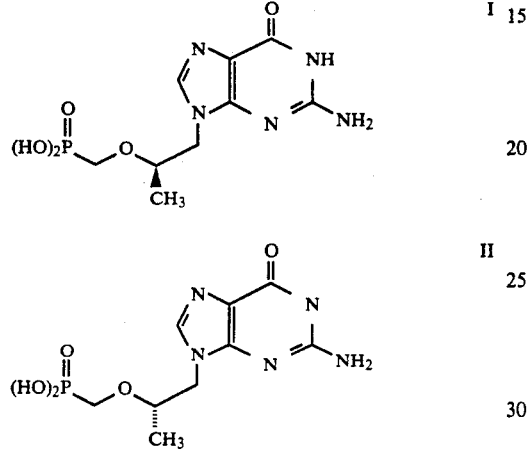

The compounds of the present invention also exhibit antiviral activity without observable cytotoxicity and, thus, can advantageously be used in the treatment of viral infections. In particular, these compounds are effective against human immunodeficiency virus (HIV). The most preferred compound of the present invention is the chiral (R)-isomer of Formula I which, surprisingly, exhibits complete cell protection against HIV over a broad concentration range with no observable cytotoxicity.

The present invention, as indicated, also pertains to the pharmaceutically acceptable non-toxic salts of the compounds of Formulas I and II. Such physiologically acceptable salts may include those derived by combination of appropriate cations such as alkali and alkaline earth metal ions or ammonium and quaternary amino ions with the acid anion moiety of the phosphonic acid group. Additionally, salts may be formed from acid addition of certain organic and inorganic acids with basic centers of the purine, specifically guanine, base. Finally, it is to be understood that the compounds of the present invention can exist in various tautomeric forms, in their unionized as well as zwitterionic form and/or in the form of solvates, which are all considered to be included within the scope of the present invention The compounds of Formulas I and II can be prepared by a sterospecific synthesis following the general procedures illustrated in Reaction Schemes 1 and 2, respectively The procedures for the preparation of compounds of Formulas I and II are similar, except for the use of opposite enantiomeric (chiral) starting materials of Formulas IIIa and IIIb.

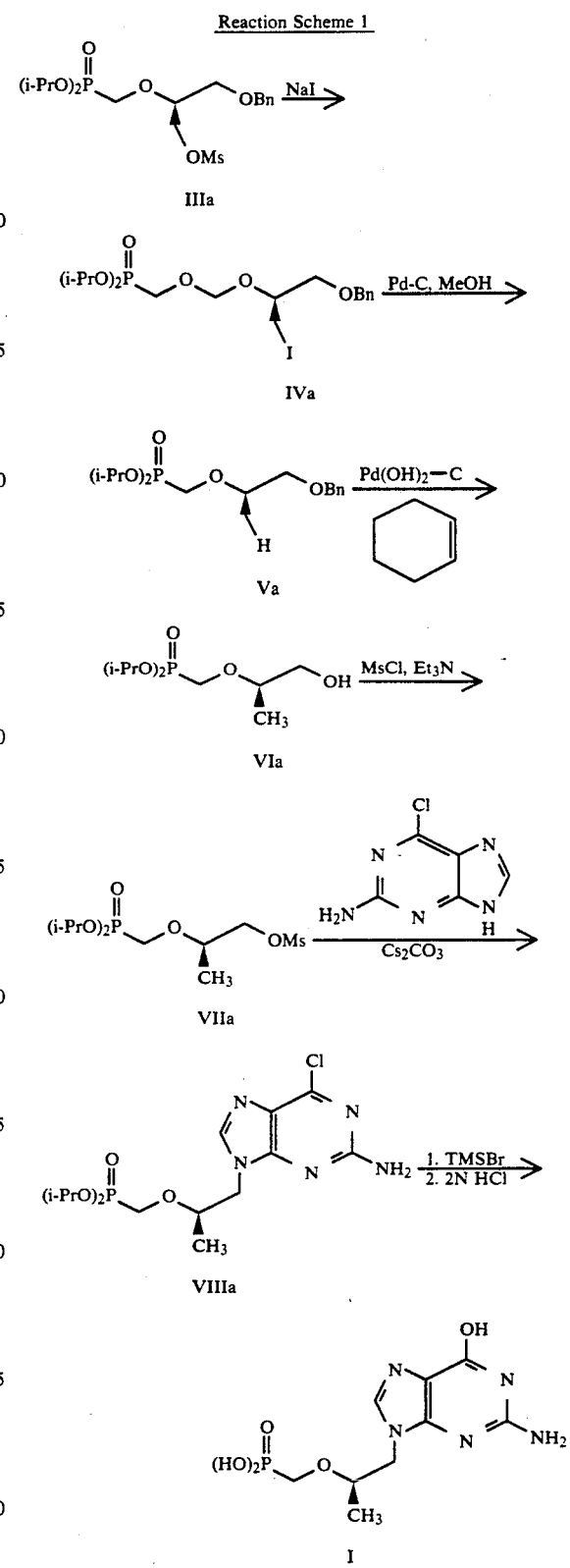

The preparation of the chiral (R)-isomer of Formula I is illustrated in Reaction Scheme 1 starting with the completely protected phosphonate ester of Formula IIIa which is prepared from chiral (S)-2,3-O-isopropylidene glycerol following the procedure described by J.

J. Bronson, et al., in *J. Med. Chem.*, 1989, 32. 1457, except that the phosphonate is protected with an isopropyl instead of an ethyl group. In contrast to the previous use of starting material of Formula IIIa, wherein the mesylate group is utilized as a leaving group, in this instance, the mesylate is converted to the iodo compound of Formula IVa with sodium iodide in an inert organic solvent such as acetonitrile, acetone, and the like at the reflux temperature of the solvent. The desired methyl substituent of the compound of Formula Va having the desired stereochemical configuration is advantageously produced from the iodo compound of Formula IVa by catalytic hydrogenation using, for example, palladium on carbon. The benzyl protecting group of the compound of Formula Va is then selectively removed by catalytic hydrogenolysis using palladium hydroxide on carbon in an organic medium containing cyclohexene. The resulting primary alcohol of Formula VIa is then converted to an organic leaving group such as halide, tosylate, mesylate, and triflate in the presence of an organic base. Advantageously, the reaction is carried out with methylsulfonyl chloride and triethylamine to give the mesylate of Formula VIIa. The alkylation of 2-amino-6-chloropurine is carried out in a coupling reaction with the mesylate of Formula VIIa in an inert organic solvent such as acetonitrile, dimethylformamide, and the like in the presence of an excess of inorganic bases such as cesium carbonate or sodium hydride. The completely protected phosphonate ester of Formula VIIIa is first treated with bromotrimethylsilane and then the intermediate is hydrolyzed in an acidic medium, for example, 2N hydrochloric acid, to produce the optically active (R)-isomer of Formula I.

Reaction Scheme 2

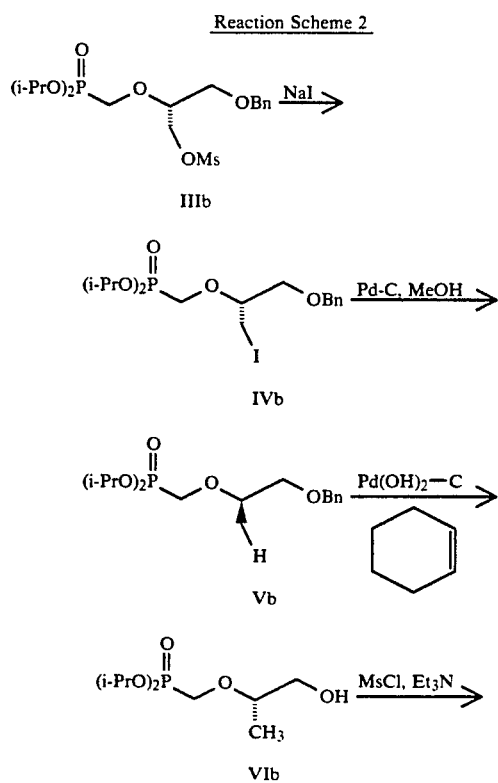

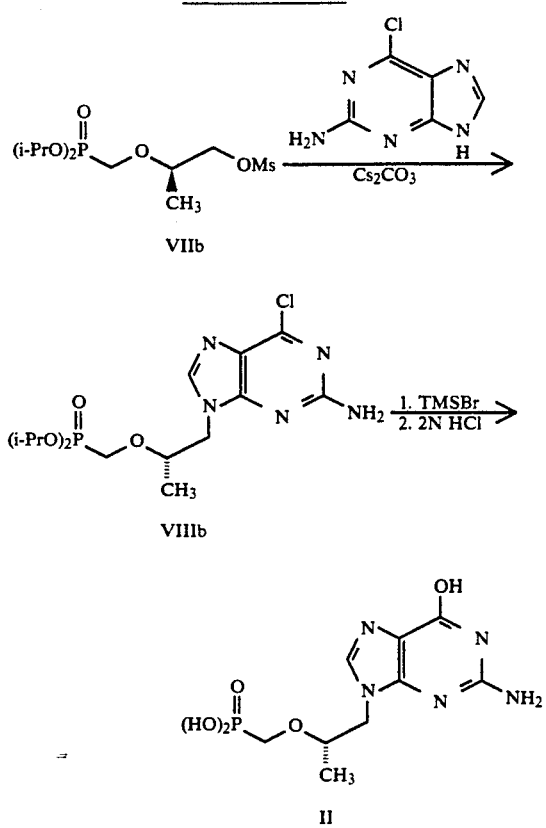

The preparation of the chiral (S)-isomer of Formula II is illustrated in Reaction Scheme 2 starting with the completely protected phosphonate ester of Formula IIIb which is prepared from chiral (R)-2,3-O-isopropylidene glycerol following the procedure described by J. J. Bronson, et al., in *J. Med. Chem.*, 1989, 32, 1457, except that the phosphonate is protected with an isopropyl instead of an ethyl group. The optically active (S)-isomer of Formula II is prepared from the phosphonate ester of Formula IIIb as shown in Reaction Scheme 2 following the same general procedures and reaction sequences as illustrated in Reaction Scheme 1 for the preparation of the (R)-isomer of Formula I.

Reaction Scheme 3

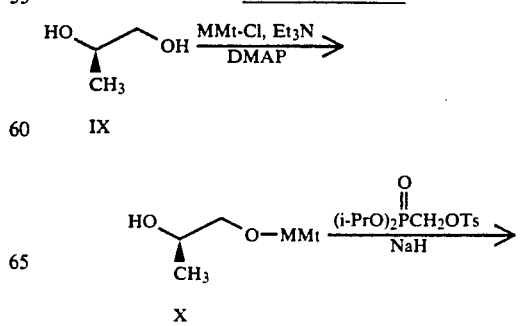

-continued
Reaction Scheme 3

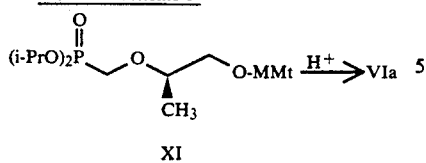

XI

In an alternate procedure for the preparation of the (R)-isomer of Formula I, the chiral intermediate of Formula VIa may be prepared starting with (S)-1,2-propanediol of Formula IX, as illustrated in Reaction Scheme 3. The primary alcohol of the compound of Formula IX can selectively be protected with p-anisyl-chlorodiphenylmethane (MMt-Cl) in the presence of dimethylaminopyridine and triethylamine to produce the compound of Formula X. The secondary alcohol of Formula X is then alkylated with diisopropyl tosyloxymethanephosphonate to give the intermediate of Formula XI which is then hydrolyzed with acid to produce the chiral intermediate of Formula VIa.

In view of the unexpected biological activity observed with the compounds of the present invention, applicants wished to compare the HIV activity of the instant compounds with the activity of the preferred compounds described in European Patent Application EP-269,947 and the similarly disclosed compound of European Patent Application EP-253,412. Previous reports have indicated that the antiviral activity of nucleoside and nucleotide analogs may reside in only one of the isomers which contain a chiral center. However, European Patent Application EP-253,412 discloses the preparation of the racemic (RS) mixture while European Patent Application EP-269,947 discloses the preparation of the (S)-isomer of the compounds the present applicants wished to compare. Accordingly, it was necessary for the present applicants to prepare the (R)- and (S)-isomers of 9-[3-hydroxy-2-(phosphonomethyl)-propyl]guanine, also designated as HPMPG, in order for a direct comparison to be made. Reaction Schemes 4 and 5 illustrate the stereospecific synthesis which was used to prepare the (R)-isomer and (S)-isomer of HPMPG, respectively.

-continued
Reaction Scheme 4

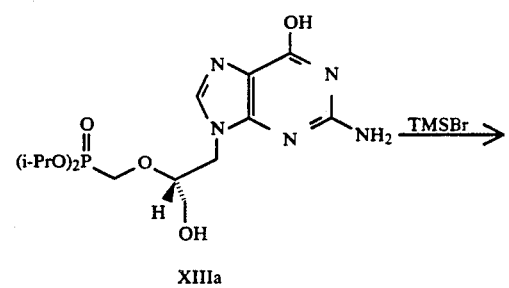

XIIIa

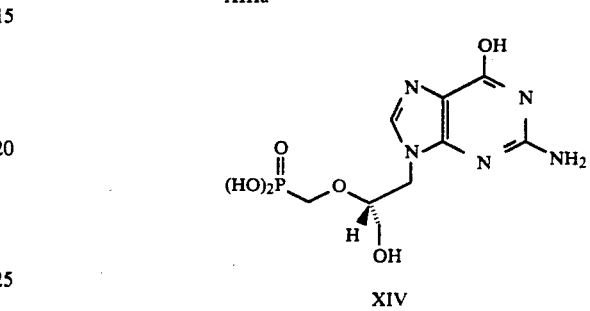

XIV

The compound of Formula XIV [(R)-HPMPG] may be prepared from the compound of Formula IIIa, as illustrated in Reaction Scheme 4. Thus, the intermediate of Formula IIIa is treated with 6-O-benzylguanine in the presence of an inorganic base such as cesium carbonate in an inert organic solvent to produce the coupled alkylated product of Formula XIIa. Subsequent removal of the benzyl protecting groups was carried out by catalystic hydrogenolysis using palladium hydroxide on carbon in the presence of cyclohexene to produce the intermediate of Formula XIIIa. The phosphonate ester of Formula XIIIa is treated with trimethylsilylbromide to produce the optically active (R)-HPMPG of Formula XIV.

Reaction Scheme 4

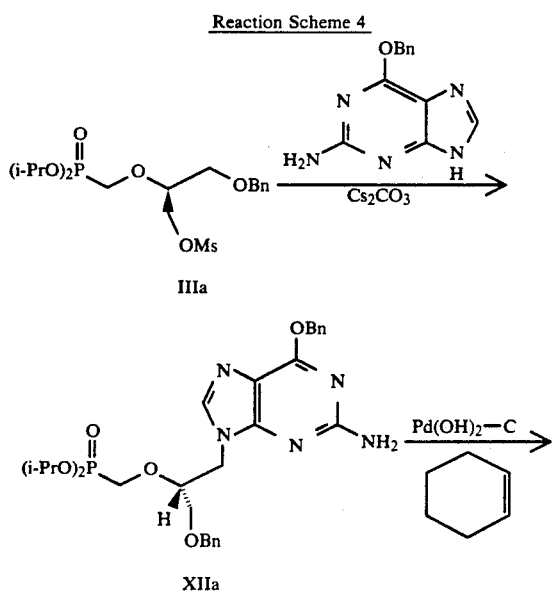

IIIa

XIIa

Reaction Scheme 5

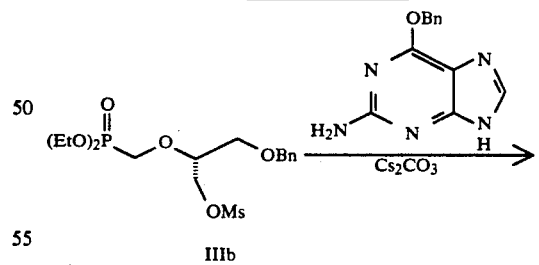

IIIb

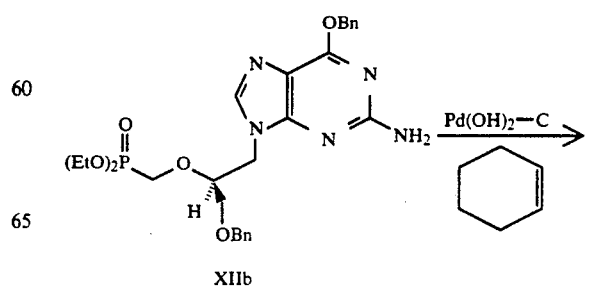

XIIb

-continued
Reaction Scheme 5

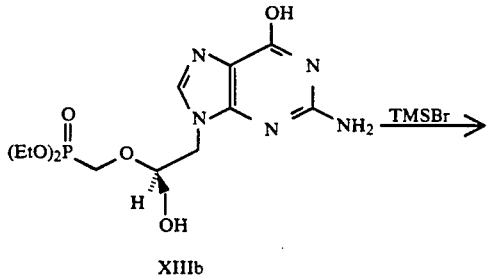

XIIIb

[Structure XV shown: phosphonomethoxy compound with guanine base]

XV

The compound of Formula XV [(S)-HPMPG] may be prepared from the compound of Formula IIIb, as illustrated in Reaction Scheme 5. The starting material of Formula IIIb is coupled with 6-O-benzylguanine to give the intermediate of Formula XIIb and then removal of the benzyl groups followed by hydrolysis of the phosphonate ester of Formula XIIIb, similar to the procedures used in Reaction Scheme 4, to produce the optically active (S)-HPMPG of Formula XV.

Pharmaceutically acceptable salts of a Formula I or II compound of this invention are prepared by methods known in the art. The salts include ammonium salts and salts of physiologically acceptable metals, particularly $Li^+$, $K^+$, $Na^+$, $Ca^{++}$, $Mg^{++}$, and comprise a further aspect of the invention. Metal salts can be prepared by reacting the metal hydroxide with a Formula 1 or II compound of this invention. Examples of metal salts which can be prepared in this way are salts containing $Li^+$, $Na^+$, and $K^+$. A less soluble metal salt can be precipitated from the solution of a more soluble salt by addition of the suitable metal compound. Acid salts may be prepared by reacting a Formula I or II compound of the invention with an inorganic or organic acid, e.g., HCl, HBr, $H_2SO_4$, organic sulfonic acids, and the like.

ABBREVIATIONS OF COMPOUNDS

The abbreviations used to identify the compounds of this nucleotide class are well-known in the art and are used herein as defined below.

| | |
|---|---|
| PMEG: | 9-[2-(phosphonomethoxy)ethyl]-guanine (compound of Example 7 in European Patent Application EP-269,947 and compound 5 in TABLE 2 of European Patent Application EP-253,412) |
| (R)-2'-methyl-PMEG: | (R)-9-[2-(phosphonomethoxy)propyl]guanine (compound of Example 7) |
| (S)-2'-methyl-PMEG: | (S)-9-[2-(phosphonomethoxy)propyl]guanine (compound of Example 13) |
| (R)-HPMPG: | (R)-9-[3-hydroxy-2-(phosphonomethoxy)propyl]guanine (compound of Example 16) |
| (S)-HPMPG: | (S)-9-[3-hydroxy-2-(phosphonomethoxy)propyl]guanine (compound of Example 19) |

BIOLOGICAL ACTIVITY

To illustrate the antiviral activity against both herpes viruses and, in particular, human immunodeficiency virus (HIV), the compounds of the instant invention and a representative number of known compounds are presented in Tables I and II and FIGS. 1-7, along with their relative cytotoxicities.

In Vitro Antiviral Activity

The compounds were evaluated for antiviral activity in vitro by the standard plaque reduction assay. Experiments were conducted with vero cells (African Green Monkey Kidney cells) infected with herpes simplex virus Type 1 (HSV-1) [BW$^s$ strain, C. D. Sibrack, et al., Infect. Dis., 1982, 146, 673] and herpes simplex virus Type 2 (HSV-2) [G strain, obtained from American Tissue Culture Collection, Rockville, Md.] and with MRC-5 cells (human embryonic lung (diploid) cells) infected with human cytomegalovirus (HCMV) [AD169 strain, obtained from American Tissue Culture Collection, Rockville, Md.].

Briefly, confluent cell monolayers in 24-well plates were infected with 30-50 plaque-forming units of virus in 100 μl of phosphate-buffered saline. After a 1 hour adsorption period, residual inoculum was replaced with 1 mL of the appropriate dilution of the test compound which had been freshly prepared in Eagle's minimal essential medium (EMEM) containing 10% fetal bovine serum. After a 48 hour incubation period at 37° C. in a 5% $CO_2$ atmosphere, cell monolayers were fixed and stained with Carbol fuchsin and plaques were counted. The antiviral potency of the compound was determined by $IC_{50}$, the inhibitory concentration necessary to reduce the number of plaques by 50% of those in the virus control cultures. The antiviral activities of the test compounds against HSV-1, HSV-2, and HCMV are shown in Table 1.

TABLE 1

| Compound | $IC_{50}$ (μg/mL) | | |
|---|---|---|---|
| | HSV-1[a] | HSV-2[a] | HCMV[b] |
| PMEG | 0.09 | 0.31 | <0.1 |
| (R)-2'-methyl-PMEG | — | 25 | 5.0 |
| (S)-2'-methyl-PMEG | — | 25 | 5.0 |
| (R)-HPMPG | 32 | 32 | 0.5 |
| (S)-HPMPG | 8 | 31 | 0.9 |

[a] In vero cells.
[b] In MRC-5 cells.

ASSAYS WITH HUMAN IMMUNODEFICIENCY VIRUS (HIV)

Compounds were evaluated for activity against human immunodeficiency virus ($LAV_{BRU}$ strain obtained from Luc Montagnier, Institut Pasteur, Paris, France) in CEM-SS cells (P. L. Nara, et al., in AIDS Res. Human. Retroviruses, 1987, 3, 283-302) or in MT-4 cells (S. Harada, et al., in Science, 1985, 229, 563-566) using the XTT assay described by O. S. Weislow, et al., in J. Natl. Cancer Instit., 1989, 81, 577-586. CEM-SS cells were obtained from Owen Weislow at the National Cancer Institute, and MT-4 cells were obtained from Doug Richman at the University of California at San Diego. Cells were exposed to HIV and cultured in microtiter plates in the presence of test compounds at concentrations of 0.0013, 0.0064, 0.032, 0.16, 0.8, 4, 20, 100, and 500 µM. On day 7 post-infection, the antiviral effect was measured using the XTT assay in which an optical density (OD) reading is obtained at each drug concentration. The optical density reading is proportional to the number of viable cells. Plots of drug concentration versus optical density readings are shown in FIGS. 1–7. Assays run in infected cells show the antiviral effect of the test compounds, where an increase in the number of viable cells (higher OD reading) reflects the protective, antiviral activity of the compound. Assays run in uninfected cells provide a measure of cellular toxicity.

The antiviral effect is also expressed (see Table 2) as the concentration of compound which increases the number of viable cells in infected cultures to 50%, that of the untreated, uninfected control cultures ($ED_{50}$). The cellular toxicity is expressed as the concentration of compound which reduces the number of viable cells to 50%, that of the untreated control ($TD_{50}$). The selectivity index (SI) is the ratio of $TD_{50}$ to $ED_{50}$.

The anti-HIV activity and cellular toxicity of the test compounds are plotted in FIGS. 1–7 as a function of optical density verus increasing log concentrations of the test compounds (XTT assay). FIGS. 1–7 visually show the results of the relative anti-HIV activity of the test compounds on infected cells ( - ) against the cellular toxicity of the same test compound on uninfected cells (■-■) against the cellular toxicity of the same test compound on uninfected cells (□-□).

Figure 2:
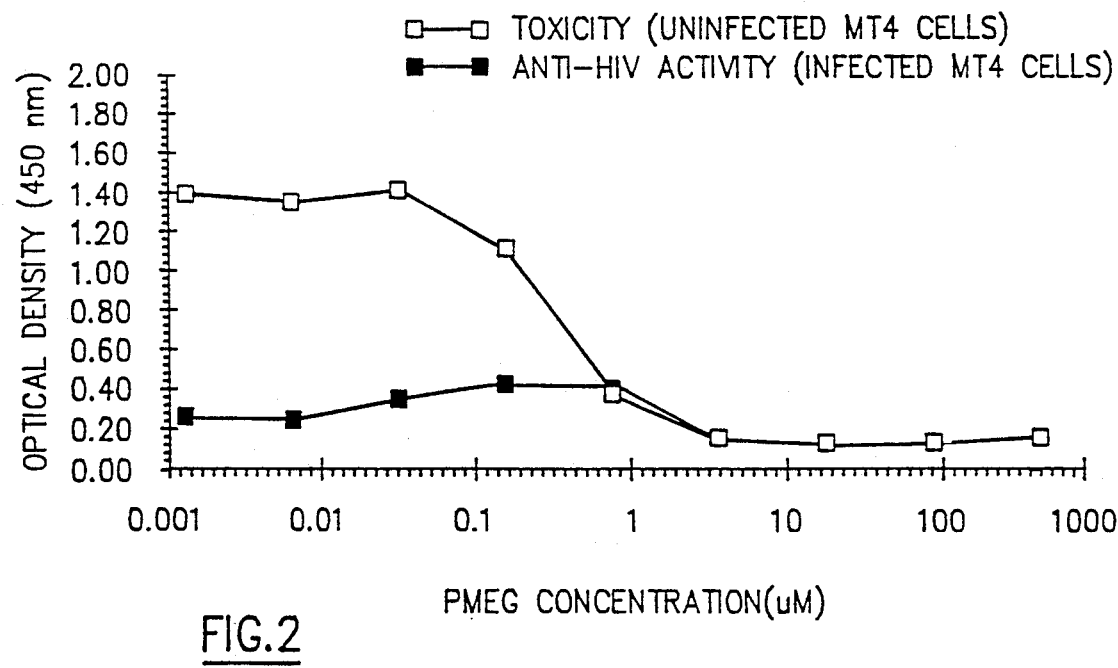
FIG. 2 illustrates the relative effects between cellular toxicity of uninfected and anti-HIV activity of infected MT4 cells by increasing concentrations of PMEG.
Figure 3:
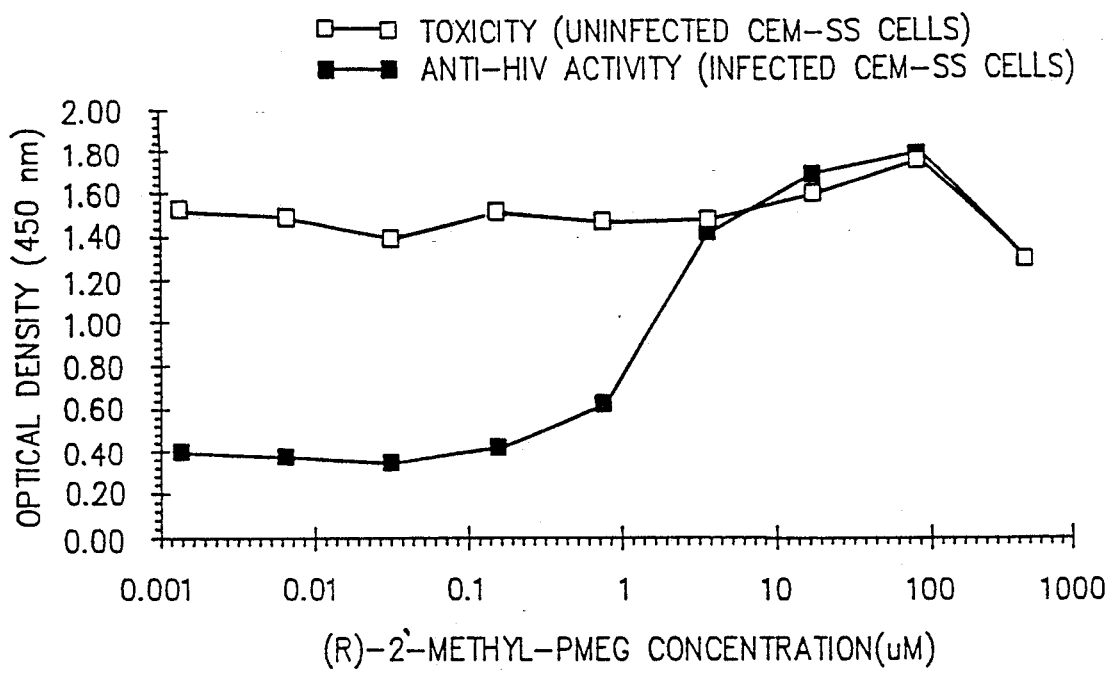
FIG. 3 illustrates the relative effects between cellular toxicity of uninfected and anti-HIV activity of infected CEM-SS cells by increasing concentrations of (R)-2'-methyl-PMEG (Compound I).
Figure 4:
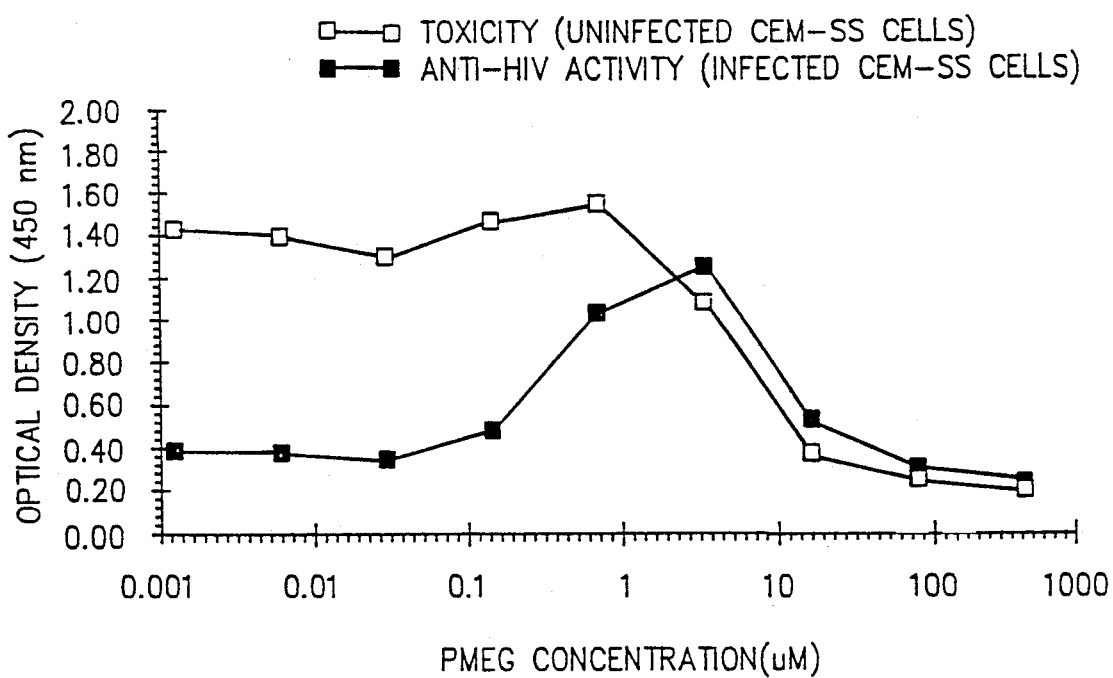
FIG. 4 illustrates the relative effects between cellular toxicity of uninfected and anti-HIV activity of infected CEM-SS cells by increasing concentrations of PMEG.
Figure 5:
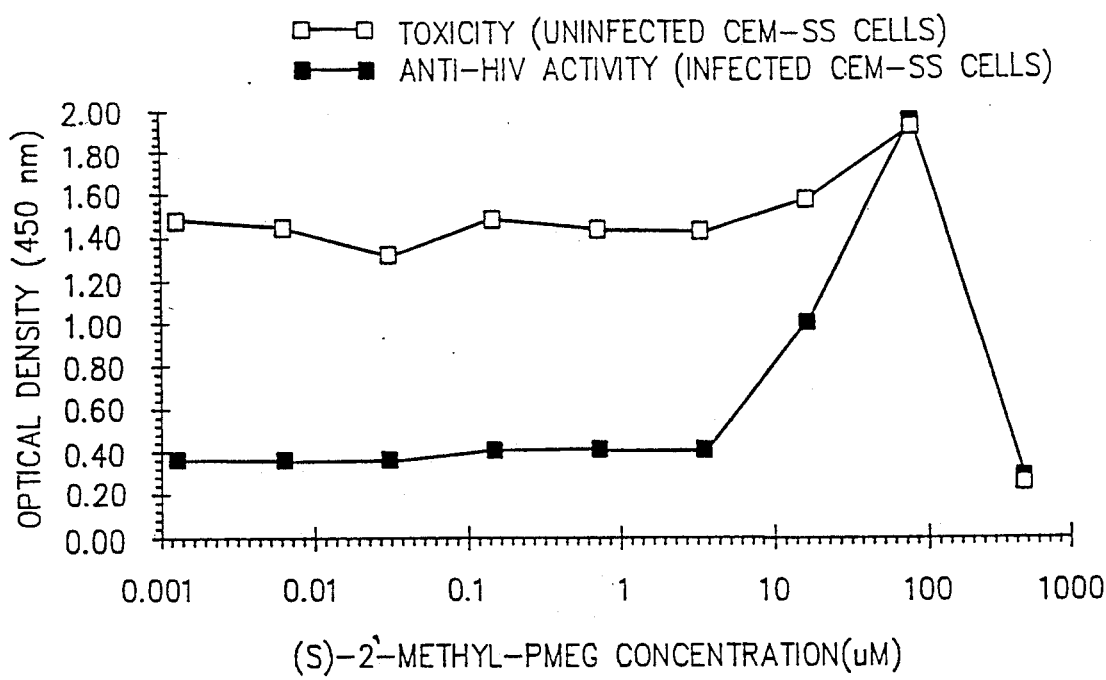
FIG. 5 illustrates the relative effects between cellular toxicity of uninfected and anti-HIV activity of infected CEM-SS cells by increasing concentrations of (S)-2'-methyl-PMEG (Compound II).
Figure 6:
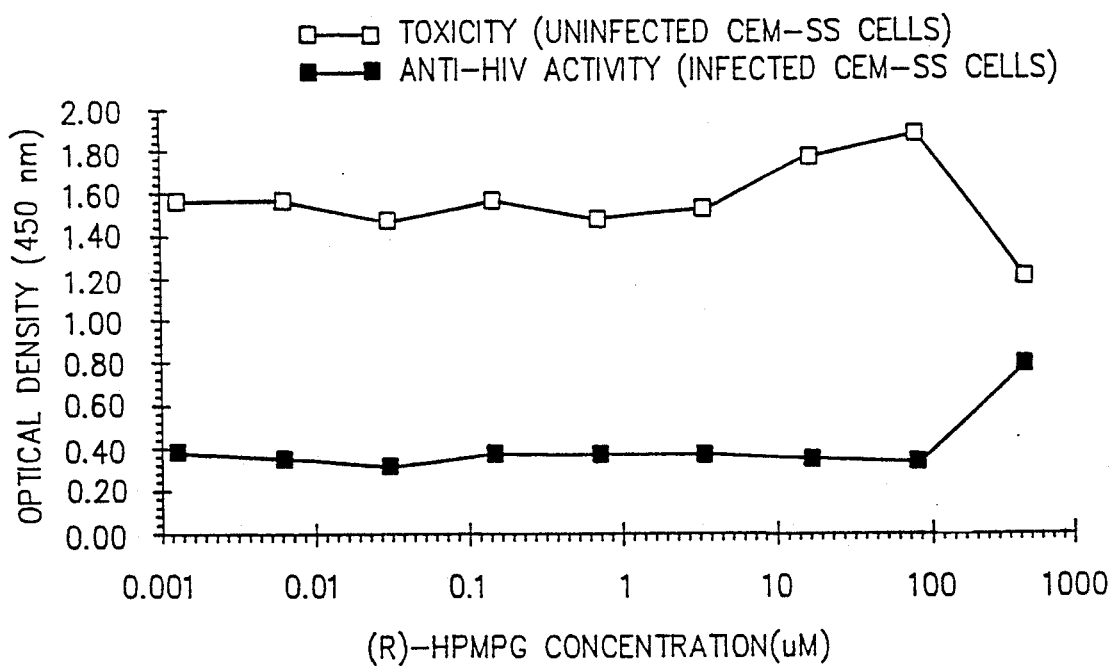
FIG. 6 illustrates the relative effects between cellular toxicity of uninfected and anti-HIV activity of infected CEM-SS cells by increasing concentrations of (R)-HPMPG.
Figure 7:
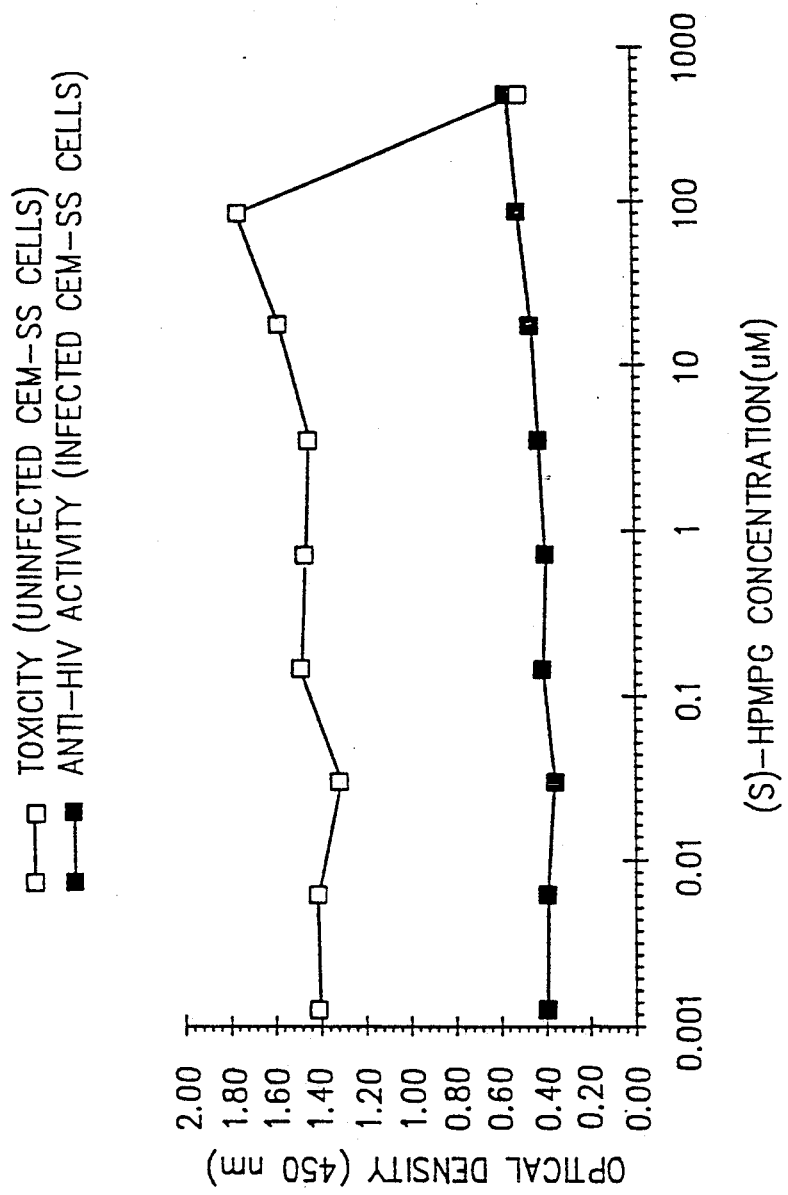
FIG. 7 illustrates the relative effects between cellular toxicity of uninfected and anti-HIV activity of infected CEM-SS cells by increasing concentrations of (S)-HPMPG.

The anti-HIV activity of the (R)-isomer (R)-2'-methyl-PMEG of the instant invention is shown in FIG. 1 (MT4 cells) and FIG. 3 (CEM-SS cells) while the (S)-isomer (S)-2'-methyl-PMEG is shown in FIG. 5 (CEM-SS cells). The anti-HIV activity of the comparison compound PMEG is shown in FIG. 2 (MT4 cells) and FIG. 4 (CEM-SS cells) while the results of the anti-HIV assay of the (R)- and (S)-HPMPG are shown in FIGS. 6 and 7 (CEM-SS cells), respectively.

FIGS. 1 and 3 show that, over a concentration range of 5 to 100 µM, (R)-2'-methyl-PMEG provides complete protection from the human immunodeficiency virus in both MT4 and CEM-SS cell lines with no observed cellular toxicity at concentrations less than 100 µM. FIG. 5 shows that (S)-2'-methyl-PMEG provides complete protection from HIV in CEM-SS cells at 100 µM with no observed cellular toxicity at concentrations less than 100 µM. By comparison, as shown in FIG. 2, PMEG is highly toxic to MT4 cells at concentrations above 0.1 µM, and no anti-HIV effect can be measured due to the cellular toxicity of PMEG. Although PMEG does exhibit some anti-HIV effect in CEM-SS cells, the cellular toxicity of PMEG once again prevents protection from the virus. Furthermore, by comparison, both (R)- and (S)-HPMPG are clearly inactive against HIV in CEM-SS cells as shown in FIGS. 6 and 7, respectively.

Selectivity Index of Test Compounds

Another estimate of the effectiveness of a compound for use against HIV in the prevention and/or treatment of AIDS is a selectivity index (an in vitro "therapeutic index"), the ratio of the effective dose to the toxic dose. The selectivity index (SI) for (R)- and (S)-2'-methyl-PMEG of the instant invention and for the comparison compounds PMEG and (R)- and (S)-HPMPG are shown in Table 2. The data in Table 2 clearly shows that (R)-2'-methyl-PMEG is both a potent and selective anti-HIV agent as compared to the other compounds having a selectivity index greater than 500.

TABLE 2

| Anti-HIV Data for PMEG, (R)- and (S)-2'-methyl-PMEG, and (R)- and (S)-HPMPG in CEM-SS Cells Evaluated by XTT Assay | | | |
|---|---|---|---|
| Compound | $ED_{50}$ (µM)[a] | $TC_{50}$ (µM)[b] | SI[c] |
| PMEG | 0.2 | 15 | 30 |
| (R)-2'-methyl-PMEG | 1 | >500 | >500 |
| (S)-2'-methyl-PMEG | 12 | 300 | 25 |
| (R)-HPMPG | 500 | >500 | >1 |
| (S)-HPMPG | NA[d] | 350 | — |

[a] Effective Dose 50: In infected cells, concentration of compound which results in an increase in the number of viable cells to 50% that of uninfected control.
[b] Toxic Dose 50: In uninfected cells, concentration of compound which results in a 50% decrease of viable cells.
[c] Selectivity Index: Ratio of $TD_{50}$ to $ED_{50}$.
[d] NA: Not active at concentrations up to 500 µM.

The invention, accordingly, provides compounds of Formulas I and II and their pharmaceutically acceptable salts and solvates thereof and, preferably, the compound of Formula I which is substantially free of the (S)-isomer and its pharmaceutically acceptable salts and solvates thereof for use in the therapy or prophylaxis of viral infections, especially human immunodeficiency virus, in a human subject.

The compounds of this invention, including the pharmaceutically acceptable salts and solvates thereof, have desirable antiviral activity. They exhibit activity against DNA viruses and retroviruses. In particular, the compound of Formula I exerts a significant anti-HIV effect with no observed cytotoxicity.

For use against viral infections, the compounds of this invention may be formulated into pharmaceutical preparations in any convenient way, and the invention, therefore, also includes, within its scope, pharmaceutical compositions comprising a compound of Formulas I or II or a pharmaceutically acceptable salt or solvate thereof adapted for use in human medicine. Such compositions may be presented for use in conventional manner in admixture with one or more pharmaceutically acceptable carriers or excipients. The reference *Remington's Pharmaceutical Sciences*, 15th Edition, by E. W. Martin (Mark Publishing Company, 1975), discloses typical carriers and methods of preparation.

For antiviral purposes, the compounds may be administered topically or systemically. By systemic administration is intended oral, rectal, and parenteral (i.e., intramuscular, intravenous, subcutaneous, and nasal) routes. Generally, it will be found that, when a compound of the present invention is administered orally, a larger quantity of the reactive agent is required to produce the same effect as the smaller quantity given parenterally. In accordance with good clinical practice, it is preferred to administer the instant compounds at a concentration level that will produce effective antiviral without causing any harmful or untoward side effects.

Therapeutically and prophylactically the instant compounds are given as pharmaceutical compositions comprised of an effective antiviral amount of a compound of Formulas I or II or a pharmaceutically acceptable salt thereof and a pharmaceutically acceptable carrier, as stated hereinabove. Pharmaceutical compositions for effecting such treatment will contain a major or minor amount, e.g., from 95% to 0.5% of at least one compound of the present invention in combination with a pharmaceutical carrier, the carrier comprising one or more solid, semi-solid, or liquid diluents, fillers, and formulation adjuvants which are non-toxic, inert, and pharmaceutically acceptable. Such pharmaceutical compositions are preferable in dosage unit form; i.e., physically discreet units containing a predetermined amount of the drug corresponding to a fraction or multiple of the dose which is calculated to produce the desired therapeutic response. Other therapeutic agents can also be present. Pharmaceutical compositions providing from about 0.1 to 500 mg of the active ingredient per unit dose are preferred and are conventionally prepared as tablets, lozenges, capsules, powders, aqueous or oily suspensions, syrups, elixirs, and aqueous solutions. Preferred oral compositions are in the form of tablets or capsules and may contain conventional excipients such as binding agents (e.g., syrup, acacia, gelatin, sorbitol, tragacanth, or polyvinylpyrrolidone), fillers (e.g., lactose, sugar, maize-starch, calcium phosphate, sorbitol, or glycine), lubricants (e.g., magnesium stearate, talc, polyethylene glycol, or silica), disintegrants (e.g., starch), and wetting agents (e.g., sodium lauryl sulfate). Solutions or suspensions of a Formula I or II compound with conventional pharmaceutical vehicles are employed for parenteral compositions, such as an aqueous solution for intravenous injection or an oily suspension for intramuscular injection. Such compositions having the desired clarity, stability, and adaptability for parenteral use are obtained by dissolving from 0.1% to 10% by weight of the active compound in water or a vehicle consisting of a polyhydric aliphatic alcohol, such as glycerine, propylene glycol, and polyethylene glycol or mixtures thereof. The polyethylene glycols consist of a mixture of non-volatile, usually liquid, polyethylene glycols which are soluble in both water and organic liquids and have molecular weights from about 200 to 1500.

Considering the biological activities possessed by the compounds of the instant invention, it can be seen that these compounds have antiviral properties particularly suited to their use in combating acquired immunodeficiency syndrome (AIDS). Thus, another aspect of the instant invention concerns a method for treating HIV infections in mammals, including humans, in need of such treatment which comprises systemic or topical administration to such mammal of an effective dose of a Formula I or II compound or a pharmaceutically acceptable salt or solvate thereof. A further aspect of the instant invention concerns a method for treating human cells infected with HIV infections which comprises systemic or topical administration to such cells of an effective dose of a Formula I or II compound or a pharmaceutically acceptable salt or solvate thereof. On the basis of testing, an effective dose could be expected to be from about 0.001 to about 30 mg/kg body weight. It is envisioned that, for clinical antiviral application, compounds of the instant invention will be administered in the same manner and use as for the reference drugs AZT, DDI, and D4T. For clinical applications, however, the dosage and dosage regimen must, in each case, be carefully adjusted, utilizing sound professional judgment by the physician and consideration of the age, weight, and condition of the patient, the route of administration, and the nature and gravity of the illness. Generally, a daily oral dose will comprise from about 0.1 to about 750 mg, preferably 10-500 mg of a Formula I or II compound administered from 1 to 3 times a day. In some instances, a sufficient therapeutic effect can be obtained at lower doses while larger doses will be required in others. It is also envisioned that a compound of Formula I or II may be administered on a weekly schedule, such as once or twice per week; the dosage to be used in such a regimen may be adjusted with due consideration of factors listed above and to maintain serum drug level at an anti-HIV effective level.

DESCRIPTION OF SPECIFIC EMBODIMENTS

In the following examples, all temperatures are given in degrees Centigrade. Melting points were recorded on an Electrothermal digital capillary melting point apparatus, and boiling points were measured at specific pressures (mm Hg), and both temperatures are uncorrected. Proton magnetic resonance ($^1$H NMR) spectra were recorded on a Bruker AM 300, or Varian Gemini 300 spectrometer. All spectra were determined in CDCl$_3$, DMSO-d$_6$, or D$_2$O unless otherwise indicated, and chemical shifts are reported in δ units downfield from the internal standard tetramethylsilane (TMS), and interproton coupling constants are reported in Hertz (Hz). Splitting patterns are designated as follows: s, singlet; d, doublet, t, triplet; q, quartet; m, multiplet; br, broad peak; and dd, doublet of doublet. Carbon-13 nuclear magnetic resonance $^{13}$C NMR) spectra were recorded on a Bruker AM 300 or Varian Gemini 300 spectrometer and were broad band proton decoupled. All spectra were determined in CDCl$_3$, DMSO-d$_6$, or D$_2$O unless otherwise indicated with internal deuterium lock, and chemical shifts are reported in δ units downfield from tetramethylsilane, relative to an internal standard. Infrared (IR) spectra were determined on a Perkin-Elmer 1800 FT-IR spectrometer from 4000 cm$^{-1}$ to 400 cm$^{-1}$, calibrated to 1601 cm$^{-1}$ absorption of a polystyrene film, and are reported in reciprocal centimeters (cm$^{-1}$). Optical rotations $[\alpha]_D^{20}$ were determined on a Perkin-Elmer 41 polarimeter in the solvents indicated. Ultraviolet spectra were determined on a Hewlett Packard 8452 diode array spectrophotometer in the solvent and concentration indicated. Mass spectra were recorded on a Kratos MS-50 or a Finnegan 4500 instrument utilizing the fast atom bombardment (FAB) or direct chemical ionization (DCI) technique. The mass data are expressed in the format: protonated parent ion (MH+).

Analytical thin-layer chromatography (TLC) was carried out on precoated silica gel plates (60F-254) and visualized using UV light, iodine vapors, and/or staining with one of the following reagents: (a) methanolic phosphomolybdic acid (2%) and heating; (b) reagent (a) followed by 2% cobalt sulphate in 5M H$_2$SO$_4$ and heating. Column chromatography, also referred to as flash column chromatography, was performed in a glass column using finely divided silica gel (32–63 μm on silica gel-H) and pressures somewhat above atmospheric pressure with the indicated solvents. Reversed phase analytical thin-layer chromatography was carried out on Analtech precoated reversed phase F (250 microns) plates and visualized using UV light or iodine vapors. Reversed phase column chromatography was performed in a glass column using Baker Octadecyl (C$_{18}$), 40 μm.

All evaporations of solvents were performed under reduced pressure. Celite is a registered trademark of the Johns-Manville Products Corporation for diatomaceous earth. As used herein, the term hexanes is a mixture of isomeric C$_6$ hydrocarbons as specified by the American Chemical Society, and the term "inert" atmosphere is an argon or nitrogen atmosphere unless otherwise indicated.

EXAMPLE 1

(R)-3-O-Benzyl-2-O-[(diisopropylphosphono)methyl]-1-O-(methanesulfonyl)glycerol

The title compound was prepared from (S)-2,3-O-isopropylidene glycerol following the procedure described by J. J. Bronson, et al., in *J. Med. Chem.*, 1989, 32, 1457.

$^1$H NMR (CDCl$_3$, 300 MHz) δ 7.25-7.38 (m, 5 H, PhH), 4.63-4.77 (m, 2 H, 2×POCH), 4.51 (s, 2 H, OCH$_2$Ph), 4.39 (dd, J=3.6, 11.2 Hz, 1 H, CH$_2$OMs), 4.29 (dd, J=5.7, 11.2 Hz, 1 H, CH$_2$OMs), 3.90 (dd, J=8.8, 13.7 Hz, 1 H, OCH$_2$P), 3.84-3.91 (m, 1 H, 2-CH), 3.83 (dd, J=8.7, 13.7 Hz, 1 H, OCH$_2$P), 3.61 (dd, J=5.0, 10.1 Hz, 1 H, CH$_2$OBn), 3.56 (dd, J=5.5, 10.1 Hz, 1 H, CH$_2$OBn), 3.03 (s, 3 H, CH$_3$SO$_2$), and 1.27-1.32 (m, 12 H, 4×POCHCH$_3$).

$^{13}$C NMR (CDCl$_3$, 75 MHz) δ: 137.7, 128.7, 128.1, 127.9, 78.4 (d, $^3J_{c,p}$=11 Hz, C-2), 73.5 (CH$_2$Ph), 71.2 (t, $^2J_{c,p}$=5 Hz, POCH), 69.2 and 68.2 (CH$_2$OBn and CH$_2$OMs), 65.1 (d, $^1J_{c,p}$=169 Hz, OCH$_2$P), 37.3 (CH$_3$SO$_2$), 23.9 (d, $^3J_{c,p}$=5 Hz, POCHCH$_3$), and 23.8 (d, $^3J_{c,p}$=4 Hz, POCHCH$_3$).

MS (methane, DCI) m/e: 439 (MH+).

Anal. Calcd. for C$_{18}$H$_{31}$O$_8$PS: C, 49.31; H, 7.13; Found: C, 49.16; H, 7.09.

EXAMPLE 2

(S)-1-(Benzyloxy)-2-[(diisopropylphosphono)methoxy]-3-iodopropane

A mixture of (R)-3-O-benzyl-2-O-[(diisopropylphosphono)methyl]-1-O-(methanesulfonyl)glycerol (10.0 g, 22.8 mmol) and sodium iodide (5.15 g, 34.4 mmol) in 70 mL of acetone was heated at reflux for 14 hours. The mixture was concentrated to about 30 mL volume, and insoluble material was removed by filtration. The filtrate was concentrated in vacuo, and the residue was purified by flash chromatography on silica gel (methylene chloride:acetone=1:0 to 5:1) to give 9.51 g (89%) of the title compound as an oil.

[α]$_D^{20}$: −0.82° (c 2.30, CH$_3$OH).

$^1$H NMR (CDCl$_3$, 300 MHz) δ: 7.24-7.35 (m, 5 H, PhH), 4.66-4.80 (m, 2 H, 2×POCH), 4.52 (s, 2 H, OCH$_2$Ph), 3.88 (dd, J=8.7, 13.6 Hz, 1 H, OCH$_2$P), 3.82 (dd, J=8.7, 13.6 Hz, 1 H, OCH$_2$P), 3.52-3.68 (m, 3 H, CH$_2$OBn and H-2), 3.37 (dd, J=3.6, 10.5 Hz, 1 H, CH$_2$I), 3.31 (dd, J=6.0, 10.5 Hz, 1 H, CH$_2$I), and 1.23-1.34 (m, 12 H, 4×POCHCH$_3$).

$^{13}$C NMR (CDCl$_3$, 75 MHz) δ: 137.9, 128.4, 127.8, 127.7, 79.4 (d, 3J=11 Hz, C-2), 73.3 (OCH$_2$Ph), 71.1 (CH$_2$OBn), 71.0 (d, $^2J_{c,p}$=3 Hz, POCH), 64.6 (d, $^1J_{c,p}$=168 Hz, C-P), 23.7 (t, J=4 Hz, POCHCH$_3$), and 4.9 (CH$_2$I).

MS (isobutane, DCI) m/e: 471 (MH+).

EXAMPLE 3

(R)-1-O-Benzyl-2-O-[(diisopropylphosphono)methyl]-1,2-propanediol (S)-1-(Benzyloxy)-2-[(diisopropylphosphono)methoxy]-3-iodopropane (11.1 g, 23.5 mmol) was mixed with triethylamine (2.85 g, 28.2 mmol) in 15 mL of methanol. To this solution, 10% palladium on carbon (2.0 g) was added under nitrogen atmosphere. The reaction was performed in a Parr apparatus at a hydrogen pressure of 40 psi. After 3 hours, the catalyst was removed by filtration, the filtrate was concentrated, and the residue was purified by flash chromatography on silica gel (methylene chloride:acetone=1:0 to 5:1) to give 7.91 g (98%) of the title compound as an oil.

[α]$_D^{20}$: −7.28° (c 0.29, CH$_3$OH).

$^1$H NMR (CDCl$_3$, 300 MHz) δ: 7.20-7.35 (m, 5 H, PhH), 4.66-4.80 (m, 2 H, 2×POCH), 4.52 (s, 2 H, OCH$_2$Ph), 3.84 (dd, J=8.8, 13.6 Hz, 1 H, OCH$_2$P), 3.70-3.84 (m, 2 H, 2-CH and OCH$_2$P) 3.50 (dd, J=6.0, 10.2 Hz 1 H, CH$_2$OBn) 3.41 (dd, J=4.4, 10.2 Hz, 1 H, CH$_2$OBn), 1.26-1.35 (m, 12H, 4×POCHCH$_3$), and 1.16 (d, J=6.4 Hz, 3 H, H-3).

$^{13}$C NMR (CDCl$_3$, 75 MHz) δ: 138.3, 128.4, 127.7, 76.9 (d, $^3J_{c,p}$=12 Hz, C-2), 74.0 and 73.2 (CH$_2$OBn and OCH$_2$Ph), 70.8 (d, $^2J_{c,p}$=7 Hz, POCH), 63.9 (d, $^1J_{c,p}$=169 Hz, OCH$_2$P), 23.7 (q, $^3J_{c,p}$,4 Hz, POCHCH$_3$), and 16.5 (C-3).

MS (isobutane, DCI) m/e: 345 (MH+).

Anal. Calcd. for C$_{17}$H$_{29}$O$_5$P: C, 59.29; H, 8.49; Found: C, 59.26; H, 8.37.

EXAMPLE 4

(R)-2-O-[(Diisopropylphosphono)methyl]-1,2-propanediol (R)-1-O-Benzyl-2-O-[(diisopropylphosphono)methyl]-1,2-propanediol (7.75 g, 22.5 mmol) was dissolved in a mixture of cyclohexene (30 mL) and methanol (30 mL). To the solution, 20% palladium hydroxide on carbon (1.5 g) was added. The resulting mixture was heated at reflux for 16 hours, and the catalyst was removed by filtration. The filtrate was concentrated in vacuo, and the residue containing the title compound was used in the next reaction without further purification.

$^1$H NMR (CDCl$_3$, 300 MHz) δ: 4.62-4.80 (m, 2 H, 2×POCH), 3.88 (dd, J=8.0, 13.9 Hz, 1 H, OCH$_2$P), 3.67 (dd, J=9.0 Hz, 1 H, OCH$_2$P), 3.52-3.68 (m, 2 H, H-2 and CH$_2$OH), 3.46 (dd, J=7.2, 12.0 Hz, 1 H, CH$_2$OH), 2.19 (d, J=6.0 Hz, 3 H, H-3), and 1.28-1.32 (m, 12 H, 4×POCHCH$_3$).

$^{13}$C NMR (CDCl$_3$, 75 MHz) δ: 79.0 (d, $^3J_{c,p}$=10 Hz, C-2), 70.8 (d, $^2J_{c,p}$=7 Hz, POCH), 70.6 (d, $^2J_{c,p}$=7 Hz, POCH), 65.3 (C-1), 63.3 (d, $^1J_{c,p}$=170 Hz, OCH$_2$P), 23.4 (d, $^3J_{c,p}$=4 Hz, POCHCH$_3$), 23.2 (d, $^3J_{c,p}$=5 Hz, POCHCH$_3$), and 15.4 (C-3).

EXAMPLE 5

(R)-2-O-[(Diisopropylphosphono)methyl]-1-O-methanesulfonyl-1,2-propanediol (R)-2-O-[(Diisopropylphosphono)methyl]-1,2-propanediol (used crude from Example 4, 22.5 mmol) was dissolved in 50 mL of methylene chloride and cooled to 0° C. Methanesulfonyl chloride (3.11 g, 27 mmol) was added slowly to the solution, and then, triethylamine (2.54 g, 45 mmol) was added dropwise. After the addition was complete, the mixture was stirred at 0° C. for 30 minutes and then allowed to warm slowly to room temperature. Water (50 mL) and methylene chloride (150 mL) were added to the solution. The aqueous layer was extracted with methylene chloride (2×50 mL). The combined methylene chloride extracts were washed with brine and dried over magnesium sulfate. Filtration and concentration under reduced pressure gave a residue which was purified by flash chromatography on silica gel (methylene chloride:acetone=10:1 to 5:1) to provide 6.91 g of the title compound as an oil (92% yield for 2 steps).

[α]$_D^{20}$: −7.45°, (c 1.45, CH$_3$OH).

¹H NMR (CDCl₃, 300 MHz) δ: 4.52–4.69 (m, 2 H, 2×POCH), 4.10 (dd, J=3.6, 11.1 Hz, 1 H, CH₂OMs), 4.03 (dd, J=6.1, 11.1 Hz, 1 H, CH₂OMs), 3.65–3.78 (m, 2 H, OCH₂P and H-2), 3.61 (dd, J=9.3, 13.4 Hz, 1 H, OCH₂P), 2.95 (s, 3 H, CH₃SO₂), 1.20 (d, J=6.4 Hz, 12 H, 4×POCHCH₃), and 1.10 (d, J=6.5 Hz, 3 H, H-3).

¹³C NMR (CDCl₃, 75 MHz) δ: 75.3 (d, $^3J_{c,p}$=12 Hz, C-2), 72.0 (CH₂OMs), 71.1 (d, $^2J_{c,p}$=4 Hz, POCH), 71.0 (d, $^2J_{c,p}$=4 Hz, POCH), 63.72 (d, $^1J_{c,p}$=171 Hz, OCH₂P), 37.4 (CH₃SO₂), 23.4 (d, $^3J_{c,p}$=4 Hz, POCHCH₃), 23.2 (d, $^3J_{c,p}$=4 Hz, POCHCH₃), and 15.3 (C-3).

EXAMPLE 6

(R)-2-Amino-6-chloro-9-[2-[(diisopropylphosphono)methoxy]propyl]purine (R)-2-O-[(Diisopropylphosphono)methyl]-1-O-methanesulfonyl-1,2-propanediol (2.0 g, 6.02 mmol) was mixed with 2-amino-6-chloropurine (1 23 g, 7.22 mmol) and cesium carbonate (3.92 g, 12.0 mmol) in 40 mL of acetonitrile. The mixture was gently refluxed under nitrogen atmosphere for 24 hours, then allowed to cool to room temperature, and filtered. The solvent was removed under reduced pressure The residue was purified by flash chromatography on silica gel twice (first time, methylene chloride:acetone=3:1 to 0:1; second time, methylene chloride:methanol=15:1 to 10:1). The title compound (0.85 g, 35% yield) was isolated as a glassy material which was crystallized from ethyl acetate-diethyl ether: mp 133°–135° C.

$[\alpha]_D^{20}$: −41.56° (c 0.99, CH₂Cl₂).

¹H NMR (CDCl₃, 300 MHz) δ: 7.92 (s, 1 H, H-8), 5.06 (br s, 2 H, NH₂), 4.58–4.72 (m, 2 H, 2×POCH), 4.20 (dd, J=2.6, 14.3 Hz, 1 H, H-1'), 4.03 (dd, J=7.2, 14.3 Hz, 1 H, H-1'), 3.82–3.95 (m, 1 H, H-2'),3.76 (dd, J=9.2, 13.4 Hz, 1 H, OCH₂P), 3.57 (dd, J=9.8, 13.7 Hz, 1 H, OCH₂P), 1.18–1.31 (m, 15 H, POCHCH₃ and H-3').

¹³C NMR (CDCl₃) δ: 159.2, 154.2, 151.4, 144.0, 125.1, 75.9 (d, $^3J_{c,p}$=12 Hz, C-2'), 71.2 (d, $^2J_{c,p}$=7 Hz, POCH), 63.5 (d, $^1J_{c,p}$=170 Hz, OCH₂P), 47.9 (C-1'), 23.8 (d, J=Hz, POCHCH₃), and 16.3 (C-3 ).

MS (FAB) m/e: 406 (MH+).

Anal. Calcd. for C₁₅H₂₅N₅O₄PCl: C, 44.40; H, 6.14; N, 17.26; Found: C, 44.46; H, 6.14; N, 16.99.

EXAMPLE 7

(R)-9-[2-(Phosphonomethoxy)propyl]guanine [(R)-2'-methylPMEG]

(R)-2-Amino-6-chloro-9-[2-[(diisopropylphosphono)methoxy]propyl]purine (0.38 g, 0.93 mmol) was dissolved in 5 mL of acetonitrile and treated slowly with bromotrimethylsilane (1.42 g, 9.34 mmol) under nitrogen atmosphere. The reaction mixture was allowed to stir at room temperature for 14 hours, and the solvent was removed under reduced pressure The residue was dried in vacuo and then treated with acetone (10 mL) and water (2 mL). The resulting mixture was stirred at room temperature for 20 hours. The mixture was evaporated. The residue was washed with acetone and water. The resulting solid was heated gently at reflux in 10 mL of 2N HCl for 4 hours. The solution was evaporated under reduced pressure, and the residue was crystallized from water-methanol to give 0.12 g of the title compound as pale yellow crystals. The mother liquor was concentrated to provide an additional 20 mg of the title compound (total 48% yield): mp 282°–285° C.

$[\alpha]_D^{20}$: −26.74° (c 0.43, H₂O).

¹H NMR (DMSO-d₆, 300 MHz) δ: 10.58 (br s, 1 H, NH), 7.74 (s, 1 H, H-8), 6.46 (br s, 2 H, NH₂), 4.04 (dd, J=4.4, 14.3 Hz, 1 H, H-1'), 3.95 (dd, J=5.8, 14.3 Hz, 1 H, H-1'), 3.78–3.88 (m, 1 H, H-2'), 3.58 (dd, J=9.3, 13.0 Hz, 1 H, OCH₂P), 3.51 (dd, J=9.9, 13.0 Hz, 1 H, OCH₂P), and 1.02 (d, J=6.3 Hz, 3 H, H-3').

¹³C NMR (DMSO-d₆, 75 MHz) δ: 157.2, 154.0, 151.8, 138.6, 116.1, 75.4 (d, $^3J_{c,p}$=12 Hz, C-2'), 64.4 (d, $^1J_{c,p}$=152 Hz, OCH₂P), 46.5 (C-1'), and 16.8 (C-3').

MS (FAB) m/e: 304 (MH+).

UV (H₂O) λ$_{max}$: 252 nm (ε=12,300).

IR (KBr): 3700–2100 (NH and OH), 1710 (C=O), 1684, 1604 (C=C, C=N), 1104 (C-O), 1046, 994, and 952 (P-O) cm⁻¹.

Anal. Calcd. for C₉H₁₄N₅O₅P·1.25 H₂O: C, 33.18; H, 5.10; N, 21.50; Found: C, 33.18; H, 4.96; N, 21.58.

EXAMPLE 8

(R)-1-(Benzyloxy)-2-[(diisopropylphosphono)methoxy]-3-iodopropane

Sodium iodide (41.6 g, 277 mmol) was added in one portion to a solution of (R)-1-(benzyloxy)-2-[(diisopropylphosphono)methoxy]-3-(methanesulfonyloxy)-propane (prepared according to the procedure described by J. J. Bronson, et al., in J. Med. Chem., 1989, 32, 1457) (12.1 g, 27.7 mmol) in 100 mL of acetone. The reaction mixture was heated at reflux for 6 hours and then allowed to cool to room temperature. The mixture was concentrated in vacuo and partitioned between ethyl acetate (200 mL) and water (200 mL). The organic layer was washed with saturated sodium chloride solution, dried over sodium sulfate, filtered, and concentrated in vacuo to afford 12.9 g of an orange oil. Purification by column chromatography on silica gel (10:1, 75% ethyl acetate/hexane) gave 12.4 g (95%) of the title compound as a clear, colorless liquid.

$[\alpha]_D^{20}$: +0.62°, (c 1.1, CH₃OH).

¹H NMR (CDCl₃, 300 MHz) δ: 7.26–7.43 (m, 5 H, PhH), 4.67–4.79 (m, 2 H, 2×POCH), 4.52 (s, 2 H, OCH₂Ph), 3.79–3.92 (m, 2 H, OCH₂P), 3.53–3.67 (m, 3 H, H-2 and CH₂OBn) 3.29–3.39 (m, 2 H, CH₂I), and 1.29–1.33 (m, 12 H, 4×POCHCH₃).

MS (methane, DCI) m/e: 471 (MH+).

EXAMPLE 9

(S)-1-O-Benzyl-2-O-[(diisopropylphosphono)methyl]-1,2-propanediol

A solution of (R)-1-(benzyloxy)-2-[(diisopropylphosphono)methoxy]-3-iodopropane (12.0 g, 25.5 mmol) in 15 mL of methanol was treated with triethylamine (3.10 g, 30.6 mmol) and 10% palladium on carbon (2.0 g), and the mixture was placed under 40 psi hydrogen atmosphere in a Parr shaker apparatus. After 2 hours, the reaction mixture was filtered through a 1" pad of Celite, and the collected solid was washed with methanol. The filtrate was concentrated and treated with ethyl acetate (200 mL). The precipitate was removed by filtration, the filtrate was concentrated in vacuo, and the residue was purified by column chromatography on silica gel (10:1, 75% ethyl acetate/hexane) to afford 8.24 g (94%) of the title compound as a clear, colorless oil.

$[\alpha]_D^{20}$: 5.67°, (c 0.97, CH₃OH).

¹H NMR (CDCl₃, 300 MHz) δ: 7.22–7.34 (m, 5 H, PhH), 4.66–4.78 (m, 2 H, 2×POCH), 4.51 (s, 2 H, OCH₂Ph), 3.70–3.89 (m, 3 H, OCH₂P and H-2), 3.39–3.53 (m, 2 H, CH₂OBn), 1.27–1.31 (m, 12 H, 4×POCHCH₃), and 1.16 (d, J=6 Hz, 3 H, H-3).

MS (methane, DCI) m/e: 345 (MH+)

EXAMPLE 10

(S)-2-O-[(Diisopropylphosphono)methyl]-1,2-propanediol

A solution of (S)-1-O-benzyl-2-O-[(diisopropylphosphono)methyl]-1,2-propanediol (8.20 g, 23.8 mmol) in 1:1 ethanol/cyclohexene (80 mL) was treated with 20% palladium hydroxide on carbon (4.0 g), and the mixture was heated at reflux for 18 hours. The reaction mixture was then filtered through a 1" pad of Celite, and the filtrate was concentrated in vacuo to give 6.3 g of the title compound as a clear, colorless oil which was used in the following reaction without purification.

$^1$H NMR (CDCl$_3$, 300 MHz) δ: 4.66–4.81 (m, 2 H, 2×POCH), 3.89 (dd, J=8, 14 Hz, 1 H, OCHP), 3.55–3.81 (m, 3 H, OCHP, H-2, and CHOH), 3.46 (dd, J=7, 12 Hz, 1 H, CHOH), 3.10 (br s, 1 H, OH), 1.25–1.32 (m, 12 H, 4×POCHCH$_3$), and 1.10 (d, J=6 Hz, 3 H, H-3).

MS (methane, DCI) m/e: 255 (MH+).

EXAMPLE 11

(S)-2-O-[(Diisopropylphosphono)methyl]-1-O-methanesulfonyl-1,2-propanediol

Methanesulfonyl chloride (3.27 g, 28.5 mmol) was added in 1 portion to an ice-cold solution of (S)-2-O-[(diisopropylphosphono)methyl]-1,2-propanediol (used crude from Example 10, 23.8 mmol) in methylene chloride (100 mL). Triethylamine (3.61 g, 35.7 mmol) was added dropwise via syringe over 5 minutes. The resulting pale-yellow slurry was allowed to warm to room temperature and stirred further for 14 hours. The reaction mixture was poured into water (100 mL), the layers were separated, and the aqueous layer was extracted with methylene chloride (100 mL). The combined organic layers were washed with aqueous sodium bicarbonate solution (75 mL) and saturated sodium chloride solution (75 mL), dried over magnesium chloride, filtered, and concentrated in vacuo to afford 8.3 g of an orange oil. Purification by column chromatography on silica gel (10 1, 75% ethyl acetate/hexane to ethyl acetate) gave 6.49 g (82%) of the title compound as a pale-yellow oil.

[α]$_D^{20}$: +9.62°, (c 0.69, CH$_3$OH).

$^1$H NMR (CDCl$_3$, 300 MHz) δ: 4.65–4.80 (m, 2 H, 2×POCH), 4.21 (dd, J=4, 11 Hz, 1 H, CH$_2$OMs), 4.14 (dd, J=6, 11 Hz, 1 H, CH$_2$OMs), 3.68–3.88 (m, 3 H, OCH$_2$P and H-2), 3.06 (s, 3 H, CH$_3$SO$_2$), 1.30 (d, J=6 Hz, 12 H, 4×POCHCH$_3$), and 1.21 (d, J=6 Hz, 3 H, H-3).

MS (methane, DCI) m/e: 333 (MH+).

EXAMPLE 12

(S)-2-Amino-6-chloro-9-[2-[(diisopropylphosphono)methoxy]propyl]purine

2-Amino-6-chloropurine (1.40 g, 8.3 mmol) was added portionwise to a slurry of sodium hydride (0.25 g, 80% dispersion in oil, 8.3 mmol) in dimethylformamide (50 mL) at room temperature. Vigorous bubbling was noted during the addition. After 30 minutes, the clear, yellow solution was treated with a solution of (S)-2-O-[(diisopropylphosphono)methyl]-1-O-methanesulfonyl-1,2-propanediol (2.50 g, 7.5 mmol) in dimethylformamide (5 mL), and the reaction mixture was heated to 100° C. After 5 hours, the mixture was allowed to cool to room temperature and concentrated in vacuo. The residue was purified by column chromatography on silica gel (20:1, 2% to 4% to 8% methanol/methylene chloride) to provide 1.89 g (62%) of the title compound as a viscous pale yellow oil.

[α]$_D^{20}$: +48.16°, (c 1.1, CH$_3$OH).

$^1$H NMR (DMSO-d$_6$, 300 MHz) δ: 8.01 (s, 1 H, H-8), 6.88 (br s, 2 H, NH$_2$), 4.38–4.52 (m, 2 H, 2×POCH), 3.89–4.16 (m, 3 H, H-1' and H-2'), 3.77 (dd, J=9, 14 Hz, 1 H, OCH$_2$P), 3.64 (dd, J=10, 14 Hz, 1 H, OCH$_2$P), and 1.08–1.18 (m, 15 H, 4×POCHCH$_3$ and H-3').

$^{13}$C NMR (DMSO-d$_6$, 75 MHz) δ: 159.8, 154.7, 151.8, 144.2 (C-8), 125.5 (C-5), 76.3 (d, $^3$J$_{c,p}$=12 Hz, C-2'), 71.6 (d, 2J=7 Hz, POCH), 63.9 (d, $^1$J$_{c,p}$=170 Hz, OCH$_2$P), 48.3 (C-1'), 24.02 (d, $^3$J$_{c,p}$=7 Hz, POCHCH$_3$), 24.1 (d, $^3$J$_{c,p}$=7 Hz, POCHCH$_3$), and 16.7 (C-3').

MS (methane, DCI) m/e: 406 (MH+).

UV (CH$_3$OH)λ$_{max}$: 310 nm (ε=7,800), 248 nm (ε=4,700).

EXAMPLE 13

(S)-9-[2-(Phosphonomethoxy)propyl]guanine [(S)-2'-methylPMEG]

A.

(S)-2-Amino-6-bromo-9-[2-(phosohonomethoxy)-propyl]purine

A mixture of (S)-2-amino-6-chloro-9-[2-[(diisopropylphosphono)methoxy]propyl]purine (1.80 g, 4.40 mmol) in acetonitrile (15 mL) at room temperature was treated dropwise via syringe with bromotrimethylsilane (6.79 g, 44.3 mmol). The yellow solution was stirred for 16 hours and then concentrated in vacuo. The residue was coevaporated with acetonitrile (2×25 mL), placed under high vacuum for 4 hours, and then treated with water (20 mL) and acetone (100 mL). The resulting slurry was filtered and the collected material washed with acetone and diethyl ether to afford 1.30 g (81%) of the title compound as a pale-yellow solid.

$^1$H NMR (DMSO-d$_6$, 300 MHz) δ: 8.09 (s, 1 H, H-8), 6.91 (br s, 2 H, NH$_2$), 4.14 (dd, J=4, 14 Hz, 1 H, H-1'), 4.02 (dd, J=6, 14 Hz, 1 H, H-1'), 3.83–3.93 (m, 1 H, H-2'), 3.47–3.63 (m, 2 H, OCH$_2$P), and 1.03 (d, J=6 Hz, 3 H, H-3').

MS (methane, DCI) m/e: 366 (MH+).

UV (CH$_3$OH)λ$_{max}$: 312 nm (ε=7,000), 248 nm (ε=3,400).

B. (S)-9-[2-(Phosphonomethoxy)propyl]guanine

A slurry of (S)-2-amino-6-bromo-9-[2-(phosphonomethoxy)propyl]purine (1.20 g, 3.20 mmol) [from Step A] in 10% aqueous HCl solution (25 mL) was heated at reflux for 5 hours. The resulting clear, pale yellow solution was allowed to cool to room temperature and concentrated in vacuo. The residue was coevaporated with water (3×25 mL), dissolved in water to a volume of 5 mL, and treated with ethanol (100 mL). The resulting slurry was filtered, and the collected solid was dissolved in water and lyophilized to provide 0.66 g (66%) of the title compound as a white solid: mp 270°–272° C.

[α]$_D^{20}$: +34.66°, (c=0.68, H$_2$O).

$^1$H NMR (DMSO-d$_6$, 300 MHz) δ: 10.75 (s, 1 H, NH), 7.74 (s, 1 H, H-8), 6.45 (br s, 2 H, NH$_2$), 5.67 (br s, OH and H$_2$O), 4.01 (dd, J=4,14 Hz, 1 H, H-1'), 3.91 (dd, J=6,14 Hz, 1 H, H-1'), 3.77–3.82 (m, 1 H, H-2'), 3.44–3.58 (m, 2 H, OCH$_2$P), and 0.98 (d, J=6 Hz, 3 H, H-3').

13C NMR (DMSO-d$_6$, 75 MHz) δ: 157.1, 154.1, 151.9, 138.6 (C-8), 115.8 (C-5), 75.3 (d, $^3J_{c,p}$=12 Hz, C-2'), 64.5 (d, $^1J_{c,p}$=165 Hz, OCH$_2$P), 46.6 (C-1'), and 16.9 (C-3').

MS (methane, DCI) m/e: 304 (MH+).

UV (H$_2$O)λ$_{max}$: 252 nm (ε=11,000), 278 nm (ε=8,000); (0.1N NaOH)λ$_{max}$: 268 nm (ε=9,600); (0.1N HCl)λ$_{max}$: 254 nm (ε=10,600), 278 nm (ε=6,900).

Anal. Calcd for C$_9$H$_{14}$N$_5$O$_5$P.1.66 H$_2$O: C, 32.45; H, 5.19; N, 21.03; Found: C, 32.45; H, 4.73; N, 20.93.

EXAMPLE 14

(R)-6-O-Benzyl-9-[3-(benzyloxy)-2-[(diisopropylphosphono)methoxy]propyl]guanine (R)-3-O-Benzyl-2-O-[(diisopropylphosphono)methyl]-1-O-(methanesulfonyl)glycerol (13.8 g, 31.5 mmol), 6-O-benzylguanine (9.07 g, 37.8 mmol), and cesium carbonate (12.3 g, 37.76 mmol) were mixed in 150 mL of dry acetonitrile under nitrogen atmosphere. The mixture was heated gently at reflux for 16 hours. The solvent was removed under reduced pressure, and then, methylene chloride (150 mL) was added to the residue. Insoluble material was removed by filtration, and the filtrate was concentrated under reduced pressure to give a residue which was purified by flash chromatography on silica gel (first time, methylene chloride:methanol=30:1 to 10:1; second time, methylene chloride:acetone=2:1 to 0:1) to provide 10.86 g (59% yield) of the title compound as a thick mass. The product crystallized upon standing at room temperature. The solid was triturated with diethyl ether to give the title compound as white crystals: mp 75°-79° C.

[α]$_D^{20}$: +16.7° (c 1.02, CH$_2$Cl$_2$).

1H NMR (CDCl$_3$, 300 MHz) δ: 7.67 (s, 1 H, H-8), 7.45-7.52 and 7.20-7.35 (2 m, 10 H, ArH), 5.54 (s, 2 H, 6-OCH$_2$Ph), 4.84 (br s, 2 H, NH$_2$), 4.59-4.71 (m, 2 H, 2×POCH), 4.50 (s, 2 H, 3'-OCH$_2$Ph), 4.30 (dd, J=4.1, 14.4 Hz, 1 H, H-1'), 4.17 (dd, J=6.5, 14.4 Hz, 1 H, H-1'), 3.90-3.98 (m, 1H, H-2'), 3.83 (dd, J=8.7, 13.6 Hz, 1 H, OCH$_2$P), 3.75 (dd, J=8.0, 13.6 Hz, 1 H, OCH$_2$P), 3.50 (d, J=5.0 Hz, 2 H, CH$_2$OBn), and 1.16-1.32 (m, 12 H, 4×POCHCH$_3$).

13C NMR (CDCl$_3$, 75 MHz) δ: 161.2, 159.5, 154.5, 140.7, 137.7, 136.7, 128.6, 128.4, 128.3, 128.0, 127.9, 115.1, 78.8 (d, $^3J_{c,p}$=11 Hz, C-2'), 73.5 (3'-OCH$_2$Ph), 71.1 (d, $^2J_{c,p}$=5 Hz, POCH), 71.0 (d, $^1J_{c,p}$=7 Hz, POCH), 68.8 and 67.8 (C-3' and 6-O-CH$_2$Ph), 64.9 (d, $^1J_{c,p}$=168 OCH$_2$P), 43.9 (C-1'), 23.8 (d, $^3J_{c,p}$=4 Hz, POCHCH$_3$), and 23.7 (d, $^3J_{c,p}$=4 Hz, POCHCH$_3$).

MS (FAB) m/e: 584 (MH+).

Anal. Calcd for C$_{29}$H$_{38}$N$_5$O$_6$P: C, 59.68; H, 6.56; N, 11.99; Found: C, 59.29; H, 6.48; N, 12.09.

EXAMPLE 15

(R)-9-[2-[(Diisopropylphosphono)methoxy]-3-hydroxypropyl]guanine

A solution of 6-O-benzyl-9-[3-(benzyloxy)-2-[(diisopropylphosphono)methoxy]propyl]guanine (4.00 g, 5.85 mmol) in ethanol and cyclohexene (30 mL of each) was treated with 20% palladium hydroxide on carbon (1.0 g). The mixture was heated gently at reflux for 3 days. The catalyst was collected by filtration, boiled in methanol (100 mL) for 2 minutes, and the resulting slurry was filtered. The process was repeated 3 times. The combined filtrates were concentrated under reduced pressure, and the residue was purified by flash chromatography on silica gel (methylene chloride:methanol=10:1 to 5:1). The crude product was recrystallized from methanol-ethyl acetate to give 2.16 g (92% yield) of the title compound as a crystalline solid.

[α]$_D^{20}$: +23.7° (c 1.95, CH$_3$OH).

1H NMR (CD$_3$OD, 300 MHz) δ: 7.49 (s, 1 H, H-8), 4.65 (s, 2 H, NH$_2$), 4.34-4.46 (m, 2 H, 2×POCH), 4.05 (dd, J=4.0, 14.5 Hz, 1 H, H-1'), 3.95 (dd, J=6.6, 14.5 Hz, 1 H, H-1'), 3.71 (dd, J=8.9, 13.8 Hz, 1 H, OCH$_2$P), 3.63 (dd, J=9.5, 13.8 Hz, 1 H, OCH$_2$P), 3.58-3.66 (m, 1 H, H-2'), 3.39 (dd, J=5.0, 12.2 Hz, 1 H, H-3'), 3.33 (dd, J=5.0, 12.2 Hz, 1 H, H-3'), and 1.00-1.10 (m, 12 H, 4×POCHCH$_3$).

13C NMR (CD$_3$OD, 75 MHz) δ: 159.8, 155.7, 153.7, 140.9, 117.4, 81.9 (d, $^3J_{c,p}$=12 Hz, C-2'), 73.3 (d, $^2J_{c,p}$=6 Hz, POCH), 65.0 (d, $^1J_{c,p}$=169 Hz, OCH$_2$P), 61.5 (C-3'), 44.6 (C-1'), and 24.1 (d, $^3J_{c,p}$=4 Hz, POCHC$_3$).

A sample of the solid product was recrystallized from water to give crystals of the title compound Anal. Calcd. for C$_{15}$H$_{26}$N$_5$O$_6$P.0.25 H$_2$O: C, 44.28; H, 6.56; N, 17.21; Found: C, 44.23; H, 6.44; N, 17.36.

EXAMPLE 16

(R)-9-[3-Hydroxy-2-(phosphonomethoxy)propyl]guanine [(R)-HPMPG]

A solution of (R)9-[2-[(diisopropylphosphono)methoxy]3-hydroxypropyl]guanine (0.20 g, 0.50 mmol) in 5 mL of dry acetonitrile was treated with trimethylsilylbromide (0.99 g, 6.45 mmol) under nitrogen atmosphere. The resulting solution was protected from light and stirred at room temperature for 14 hours. The solvent was removed under reduced pressure, and the residue was dried under vacuum. To the residue, water (1 mL) and acetone (4 mL) were added. The mixture was stirred at room temperature overnight and then the solvent removed. The residue was triturated with methylene chloride and filtered. The collected solid was recrystallized from water-methanol to give 127 mg (80% yield) of the title compound as white crystals: mp 249° C. (dec.).

[α]$_D^{20}$: +32.3°, (c 1.11, H$_2$O).

1H NMR (DMSO-d$_6$, 300 MHz) δ: 7.73 (s, 1 H, H-8), 6.49 (br s, 2 H, NH$_2$), 4.17 (dd, J=4.1, 14.3 Hz, 1 H, H-1'), 3.98 (dd, J=6.6, 14.3 Hz, 1 H, H-1'), 3.61-3.73 (m, 1 H, H-2'), 3.64 (dd, J=8.9, 13.3 Hz, 1 H, OCH$_2$P), 3.58 (dd, J=9.3, 13.3 Hz, 1 H, OCH$_2$P), and 3.32-3.45 (m, 2 H, H-3').

13C NMR (DMSO-d$_6$, 75 MHz) δ: 157.1, 154.1, 151.6, 138.6, 115.9, 80.5 (d, $^3J_{c,p}$=10 Hz, C-2'), 65.6 (d, $^1J_{c,p}$=161 Hz, OCH$_2$P), 60.2 (C-3'), and 43.2 (C-1').

Anal. Calcd. for C$_9$H$_{14}$N$_5$O$_6$P: C, 33.48; H, 4.23; N, 21.59; Found: C, 33.86; H, 4.42; N, 21.93.

EXAMPLE 17

(S)-6-O-Benzyl-9-[3-(benzyloxy)-2-[(diethylphosphono)methoxy]propyl]guanine

Following the general procedure described in Example 14 and utilizing (S)-3-O-benzyl-2-O-[(diethylphosphono)methyl]-1-O-(methanesulfonyl) glycerol as the starting material, there was thereby produced the title compound.

[α]$_D^{20}$: −24.05°, (c 1.2, CH$_3$OH).

1H NMR (CDCl$_3$, 300 MHz) δ: 7.64 (s, 1 H, H-8), 7.23-7.49 (m, 10 H, 2×PhH), 5.52 (s, 2 H, 6-O-CH$_2$Ph), 4.87 Hz, 1 H, H-1'), 3.73-4.17 (m, 8 H, H-1', H-2', OCH$_2$P, and 2×POCH$_2$), 3.49-3.53 (m, 2H, CH$_2$OBn), 1.25 (t, J=6 Hz, 3 H, POCH$_2$CH$_3$), and 1.20 (t, J=6 Hz, 3 H, POCH$_2$CH$_3$).

$^{13}$C NMR (CDCl$_3$, 75 MHz) δ: 161.7, 159.9, 155.0, 141.2 (C-8), 138.2, 137.1, 129.1, 128.9, 128.9, 128.8, 128.5, 128.4, 115.8 (C-5), 79.4 (d, $^3J_{c,p}$=12 Hz, C-2'), 74.0 (OCH$_2$Ph), 69.3 and 68.3 (OCH$_2$Ph and C-3'), 64.6 (d, $^1J_{c,p}$=165 Hz, OCH$_2$P), 62.8 (d, $^2J_{c,p}$=6 Hz, POCH$_2$), 62.7 (d, $^2J_{c,p}$=6 Hz, POCH$_2$), 44.4 (C-1'), and 16.6 (d, $^3J_{c,p}$=6 Hz, POCH$_2$CH$_3$).

MS (methane, DCI) m/e: 556 (MH+).

UV (CH$_3$OH)λ$_{max}$: 284 nm (ε=11,100).

EXAMPLE 18

(S)-9-[3-Hydroxy-2-[(diethylphosphono)methoxy]-propyl]guanine

Following the general procedure described in Example 15 and utilizing the compound of Example 17 as the starting material, there was thereby produced the title compound.

[α]$_D^{20}$: −29.54° (c 1.3, CH$_3$OH).

$^1$H NMR (DMSO-d$_6$, 300 MHz) δ: 10.55 (s, 1 H, NH), 7.60 (s, 1 H, H-8), 6.45 (s, 2 H, NH$_2$), 4.92 (t, J=5 Hz, 1 H, exch, OH), 4.11 (dd, J=4, 15 Hz, 1 H, H-1'), 3.73–4.02 (m, H, H-1', H-2', OCH$_2$P, and 2×POCH$_2$), 3.44 (apparent t, J=5 Hz, 2 H, H-3'), 1.17 (t, J=6 Hz, 3 H, POCH$_2$CH$_3$), and 1.14 (t, J=6 Hz, 3 H, POCH$_2$CH$_3$).

$^{13}$C NMR (DMSO-d$_6$) δ: 157.4, 154.0, 151.9, 138.5 (C-8), 116.5 (C-5), 80.5 (d, $^3J_{c,p}$=12 Hz, C-2'), 63.0 (d, $^1J_{c,p}$=150 Hz, OCH$_2$P), 62.0 (d, $^2J_{c,p}$=6 Hz, POCH$_2$), 61.8 (d, $^2J_{c,p}$=6 Hz, POCH$_2$), 60.1 (C-3'), 43.4 (C-1'), and 16.2 (d, $^3J_{c,p}$=6 Hz, POCH$_2$CH$_3$).

MS (FAB) m/e: 376 (MH+).

UV (CH$_3$OH)λ$_{max}$: 254 nm (ε=12,700).

Anal Calcd for C$_{13}$H$_{22}$N$_5$O$_6$P.0.75 H$_2$O: C, 40.16; H, 6.09; N, 18.01; Found: C, 40.21; H, 5.71; N, 17.82.

EXAMPLE 19

(S)-9-[3-Hydroxy-2-(phosphonomethoxy)propyl]guanine [(S)-HPMPG]

Following the general procedure described in Example 16 and utilizing the compound of Example 18 as the starting material, there was thereby produced the title compound.

[α]$_D^{20}$: −35.83° (c 0.49, H$_2$O).

$^1$H NMR (DMSO-d$_6$, 300 MHz) δ: 11.10 (s, 1 H, NH), 8.46 (s, 1 H, H-8), 6.85 (s, 2 H, NH$_2$), 4.25 (dd, J=3, 14 Hz, 1 H, H-1'), 4.04 (dd, J=8, 14 Hz, 1 H, H-1'), and 3.23–3.74 (m, 5 H, H-2', OCH$_2$P, and 2×H-3').

$^{13}$C NMR (DMSO-d$_6$, 75 MHz) δ: 154.9, 154.7, 150.5, 138.1 (C-8), 110.9 (C-5), 79.7 (d, $^3J_{c,p}$=12 Hz, C-2'), 65.3 (d, $^1J_{c,p}$=160 Hz, OCH$_2$P), 60.1 (C-3'), and 44.5 (C-1').

MS (FAB) m/e: 320 (MH+).

UV (H$_2$O)λ$_{max}$: 252 nm (ε=10,000).

Anal. Calcd for C$_9$H$_{14}$N$_5$O$_6$P: C, 33.86; H, 4.42; N, 21.94; Found: C, 33.59; H, 4.34; N, 21.72.

EXAMPLE 20

(R)-1,2-Propanediol

The title compound can be prepared from (R)-lactic acid using a procedure similar to that of C. Melchiorre (Chem. Ind., 1976, 218).

[α]$_D^{20}$: −17.3° (neat).

EXAMPLE 21

(R)-1-O-[p-(Methoxyphenyl)diphenylmethyl]-1,2-propanediol

Triethylamine (234 g, 2.31 mol) and 4-dimethylaminopyridine (1 g, 8 mmol) were added to (R)-1,2-propanediol (80 g, 1.05 mol) in a mixture of ethyl acetate and methylene chloride (2:1, 0.8 L) under a nitrogen atmosphere. To this mixture, p-anisylchlorodiphenylmethane (356.5 g, 1.16 mol) was added at 0° C. The reaction mixture was stirred at 0° C. for 30 minutes and then at room temperature for 15 hours. The solid was removed by filtration. The filtrate was stripped of solvent, and the residue was put on a silica gel column (500 g) and eluted with a mixture of ethyl collected (366.6 g) was dried under vacuum and used without further purification.

$^1$H NMR (300 MHz, CDCl$_3$) δ: 7.45–7.15 (m, 12 H, ArH), 6.83–6.80 (M, 2 H, ArH), 4.00–3.90 (m, 1 H, H-2), 3.77 (s, 3 H, OCH$_3$), 3.10 (dd, J=3.4, 9.2 Hz, 1 H, H-1), 2.95 (dd, J=7.9, 9.2 Hz, 1 H, H-1), 2.35 (br d, 1 H, OH), 1.07 (d, J=6.4 Hz, 3 H, H-3).

$^{13}$C NMR (300 MHz, CDCl$_3$) δ: 158.8, 144.6, 135.7, 130.5, 128.0, 127.7, 127.1, 113.2, 86.3, 68.8 (1-C), 67.0 (2-C), 55.1 (OCH$_3$), 18.7 (3-C).

EXAMPLE 22

(R)-2-O-[(Diisopropylphosphono)methyl)]-1,2-propanediol

Sodium hydride (80% in mineral oil, 24 g, 0.80 mol) was added in five portions to a solution of the crude (R)-1-O-[p-(methoxyphenyl)diphenylmethyl]-1,2-propanediol (232 g, 0.66 mol) of Example 21 in 1 L of anhydrous tetrahydrofuran at 0° C. under a nitrogen atmosphere. The mixture was stirred at 0° C. for 30 minutes and then heated at reflux for 5 hours. The resulting reaction mixture was cooled to 0° C., and a solution of tosyloxymethyl diisopropylphosphonate (280 g, 0.80 mol) in 300 mL of anhydrous tetrahydrofuran was added via a cannula. The mixture was stirred in ice-bath and slowly warmed to room temperature overnight (18 hours). The resulting brown slurry was filtered through a pad of Celite and washed with methylene chloride. After the solvent was removed, the residue was filtered through a silica gel column and eluted with mixtures of ethyl acetate and hexane (1:5 to 1:0) to give a crude product of (R)-2-O-[(diisopropylphosphono)methyl)]-1-O-[p-(methoxyphenyl)-diphenylmethyl]-1,2-propanediol as an oil.

$^1$H NMR (300 MHz, CDCl$_3$) δ: 7.44 (d, J=7.0 Hz, 3 H, ArH), 7.33–7.16 (m, 9 H, ArH), 6.81 (d, J=8.1 Hz, ArH), 4.80–4.56 (m, 2 H, 2×POCH), 3.86 (dd, J=9.1, 13.6 Hz, OCH$_2$P), 3.76 and 3.88–3.76 (s over m, 4 H, OCH$_3$ and OCH$_2$P), 3.77–3.68 (m, 1 H, H-2), 3.16 (dd, J=5.9, 9.6 Hz, 1 H, H-1), 3.01 (dd, J=4.1, 9.6 Hz, 1 H, H-1), 1.32–1.27 (m, 12 H, POCHCH$_3$), 1.14 (d, J=6.1 Hz, 3 H, H-3).

$^{13}$C NMR (300 MHz, CDCl$_3$) δ: 158.6, 144.6, 135.7, 130.4, 128.5, 127.8, 126.8, 113.0, 86.2, 77.4, (d, $^3J_{c,p}$=12 Hz, C-2), 70.7 (t, $^2J_{c,p}$=6 Hz, POCH), 67.0 (1-C), 64.1 (d, $^1J_{c,p}$=169 Hz, OCH$_2$P), 54.9 (OCH$_3$), 23.8 (d, $^3J_{c,p}$=3 Hz, POCHCH$_3$), 23.7 (d, $^3J_{c,p}$=3 Hz, POCHCH$_3$), 16.8 (3-C).

10-Camphorsulphonic acid (21 g) was added to a solution of the crude (R)-2-O-[(diisopropylphosphono)-methyl)]-1-O-[p-(methoxyphenyl)diphenylmethyl]-1,2-propanediol in 1.8 L of methanol. The solution was heated at reflux for 7 hours. After the solvent was evaporated, the residue was purified by column chromatography on silica gel (first time, ethyl acetate:hexane=1:2 to 1:0 and then ethyl acetate:ethanol=10:1; second time, methylene chloride:acetone=5:1 to 0:1) to give 40.8 g (24% yield) of the title compound as an oil which is identical to the compound of Example 4.

What is claimed is:

1. A method for treating a patient infected with a retrovirus, which comprises administering to said patient a therapeutically anti-retroviral effective amount of a composition free of (S)-9-[2-(phosphonomethoxy)-propyl]-guanine which composition comprises (R)-9-[2-(phosphonomethoxy)propyl]-guanine or a pharmaceutically acceptable salt or solvate thereof, either alone or in a mixture with a pharmaceutically acceptable carrier.

2. A method for treating human cells infected with a retrovirus, which comprises administering to said cells a therapeutically anti-retroviral effective amount of a composition free of (S)-9-[2-(phosphonomethoxy)-propyl]-guanine which composition comprises (R)-9-[2-(phosphonomethoxy)propyl]-guanine or a pharmaceutically acceptable salt or solvate thereof, either alone or in a mixture with a pharmaceutically acceptable carrier.

* * * * *